United States Patent [19]

Aslanian et al.

[11] Patent Number: 5,578,616
[45] Date of Patent: Nov. 26, 1996

[54] PHENYL-ALKYL-IMIDAZOLES

[75] Inventors: Robert G. Aslanian, Rockaway; Michael J. Green, Skillman; Neng-Yang Shih, North Caldwell, all of N.J.

[73] Assignee: Schering Corporation, Kenilworth, N.J.

[21] Appl. No.: 469,941

[22] Filed: Jun. 6, 1995

Related U.S. Application Data

[63] Continuation of PCT/US94/12717 Nov. 10, 1994 which is a continuation-in-part of Ser. No. 153,231, Nov. 15, 1993, abandoned.

[51] Int. Cl.$^6$ .................... A61K 31/44; A61K 31/415; C07D 401/10
[52] U.S. Cl. .................... 514/341; 514/400; 546/272.7; 548/346.1
[58] Field of Search .................... 546/278; 548/346.1; 514/341, 400

[56] References Cited

U.S. PATENT DOCUMENTS

| 4,814,343 | 3/1989 | Cossement et al. | 514/397 |
| 4,923,865 | 5/1990 | Cossement et al. | 514/235.8 |

FOREIGN PATENT DOCUMENTS

| 0024829 | 3/1981 | European Pat. Off. |
| 0341231 | 11/1989 | European Pat. Off. |
| 0420396A2 | 4/1991 | European Pat. Off. |
| WO93/01812 | 2/1993 | WIPO |
| WO93/14070 | 7/1993 | WIPO |

OTHER PUBLICATIONS

'Derwent' Abstract [#93-243102/30] of WO 93/14070 (published 22 Jul. 1993).
'Derwent' Abstract [#89-327661/45] of JP 1242571 (published 27 Sep. 1989).
Howson et al., *Bioorg. & Med. Chem. Letters.*, vol. 2 No. 1 (1992), pp. 77–78.
Van der Goot et al., *Eur. J. Med. Chem.* (1992) vol. 27, pp. 511–517.
Clapham et al., "Ability of Histamine $H_3$ Receptor Antagonists to improve Cognition and to increase Acetylcholine Release in vivo in the Rat", British Assn. for Psychopharmacology, Jul. 25–28 1993, reported in *J. Psychopharmacol.* (Abstr. Book), A17.
Clapham et al., "Ability of the selective Histamine $H_3$ Receptor Antagonist Thioperamide to improve Short–term Memory and Reversal Learning in the Rat", *Brit. J. Pharm. Suppl.*, 1993, 110, Abstr. 65P.
Yokoyama et al., "Effect of thioperamide, a histamine $H_3$ receptor antagonist, on electrically induced convulsions in mice", *Eur. J. Pharmacol.*, vol. 234 (1993), pp. 129–133.
Donetti et al., "(Imidazolylphenyl)formamidines. A Structurally Novel Class of Potent Histamine $H_2$ Receptor Antagonists", *J. Med. Chem.*, vol. 27 (1984), pp. 380–386.
Chem. Abs. vol. 118 No. 13 (Mar. 29, 1993), Abs. #124448b.
Chem. Abs. vol. 112 No. 15 (Apr. 9, 1990), Abs. #139033n.
Chem. Abs. vol. 109 No. 25 (Dec. 19, 1988), Abs. #231016v.
Chem. Abs. vol. 120 (1994), Abs. #107004c.
J. Royal Neth. Chem. Soc. ["Recueil"], vol. 95 No. 2, pp. 45–49 (1976).
Chem. Abs. vol. 84 No. 5 (Feb. 2, 1976), Abs. #30961r.
J. Het. Chem., vol. 30 No. 6 (Dec. 1993), pp.1645–1651.
'Derwent' Abstract [#88-149329/22] of EPA 0 269 599 (published 4 Nov. 1986).

*Primary Examiner*—Jacqueline Haley
*Attorney, Agent, or Firm*—John H. C. Blasdale; Anita W. Magatti; Norman C. Dulak

[57] ABSTRACT

The invention provides novel phenyl-alkyl-imidazoles of the formula

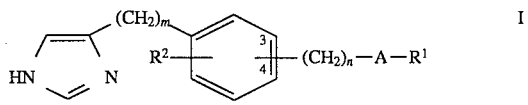

wherein A, $R^1$, $R^2$, m and n are as defined in the specification, and the group —$(CH_2)n$—A—$R^1$ is at the 3- or 4-position, together with their pharmaceutically acceptable salts. These phenyl-alkyl-imidazoles and salts have valuable pharmacological properties, especially CNS activities and activity against inflammatory disease.

21 Claims, No Drawings

PHENYL-ALKYL-IMIDAZOLES

CROSS-REFERENCE TO RELATED APPLICATIONS

This application is a continuation of International Application No. PCT/US 94/12717, filed Nov. 10, 1994, which is a continuation-in-part U.S. patent application Ser. No. 08/153,231 filed Nov. 15, 1993 abandoned.

FIELD OF THE INVENTION

The present invention relates to phenyl-alkyl-imidazoles having valuable pharmacological properties, especially CNS activities and activity against inflammatory disease. Compounds of this invention are antagonists of the $H_3$ receptor.

BACKGROUND OF THE INVENTION

European Patent Application No. 0 420 396 A2 (Smith Kline & French Laboratories Limited) and Howson et al., *Bioorg. & Med. Chem. Letters*, Vol. 2 No. 1 (1992), pp. 77–78 describe imidazole derivatives having an amidine group as $H_3$ agonists. Van der Groot et al. (*Eur. J. Med. Chem.* (1992) Vol. 27, pp. 511–517) describe isothiourea analogs of histamine as potent agonists or antagonists of the histamine $H_3$ receptor, and these isothiourea analogs of histamine overlap in part with those of the two references cited above. Clapham et al. ["Ability of Histamine $H_3$ Receptor Antagonists to improve Cognition and to increase Acetylcholine Release in vivo in the Rat", British Assn. for Psychopharmacology, Jul. 25–28 1993, reported in *J. Psychopharmacol.* (Abstr. Book), A17] describe the ability of histamine $H_3$ receptor antagonists to improve cognition and to increase release of acetylcholine in vivo in the rat. Clapham et al. ["Ability of the selective Histamine $H_3$ Receptor Antagonist Thioperamide to improve Short-term Memory and Reversal Learning in the Rat", *Brit. J. Pharm. Suppl.*, 1993, 110, Abstract 65P] present results showing that thioperamide can improve short-term memory and reversal learning in the rat and implicate the involvement of $H_3$ receptors in the modulation of cognitive function. Yokoyama et al. ["Effect of thioperamide, a histamine $H_3$ receptor antagonist, on electrically induced convulsions in mice", *Eur. J. Pharmacol.*, vol. 234 (1993), pp. 129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO9301812-A1 (SmithKline Beecham PLC) describes the use of S-[3-(4(5)-imidazolyl)propyl] isothiourea as a histamine $H_3$ antagonist, especially for treating cognitive disorders, e.g. Alzheimer's disease and age-related memory impairment. Schlicker et al. ["Novel histamine $H_3$ receptor antagonists: affinities in an $H_3$ receptor binding assay and potencies in two functional $H_3$ receptor models"] describe a number of imidazolylalkyl compounds wherein the imidazolylalkyl group is bonded to a guanidine group, an ester group or an amide group (including thioamide and urea), and compare these to thioperamide. Leurs et al. ["The histamine $H_3$-receptor: A target for developing new drugs", *Progr. Drug Res.* (1992) vol. 39, pp. 127–165] and Lipp et al. ["Pharmacochemistry of $H_3$-receptors" in *The Histamine Receptor*, eds.: Schwartz and Haas, Wiley-Liss, New York (1992), pp. 57–72] review a variety of synthetic $H_3$ receptor antagonists, and Lipp et al. (ibid.) have defined the necessary structural requirements for an $H_3$ receptor antagonist.

SUMMARY OF THE INVENTION

The present invention provides a compound of the formula

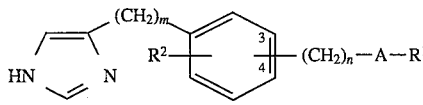

wherein:

A is selected from $-O-CO-NR^1-$, $-CO-$, $-NR^1-CO-NR^1-$, $-NR^1-CO-$, $-NR^1-$, $-O-$, $-CO-NR^1-$, $-CO-O-$, and $-C(:NR^1)-NR^1-$;

the groups $R^1$, which may be the same or different when there are two or three such groups in the molecule of formula I, are selected from hydrogen, and lower alkyl, aryl, cycloalkyl, heterocyclic and heterocyclyl-alkyl groups, and groups of the formula $-(CH_2)_y-G$, where G is selected from $CO_2R^3$, $COR^3$, $CONR^3R^4$, $OR^3$, $SR^3$, $NR^3R^4$, heteroaryl and phenyl, which phenyl is optionally substituted by halogen, lower alkoxy or polyhaloloweralkyl, and y is an integer from 1 to 3;

$R^2$ is selected from hydrogen and halogen atoms, and alkyl, alkenyl, alkynyl and trifluoromethyl groups, and groups of the formula $OR^3$, $SR^3$ and $NR^3R^4$;

$R^3$ and $R^4$ are independently selected from hydrogen, and lower alkyl and cycloalkyl groups, or $R^3$ and $R^4$ together with the intervening nitrogen atom can form a saturated ring containing 4 to 6 carbon atoms that can be substituted with one or two lower alkyl groups;

with the proviso that, when y is 1 and G is $OR^3$, $SR^3$ or $NR^3R^4$, then neither $R^3$ nor $R^4$ is hydrogen;

the group $-(CH_2)_n-A-R^1$ is at the 3- or 4-position, and the group $R^2$ is at any free position;

m is an integer from 1 to 3;

and n is 0 or an integer from 1 to 3;

or a pharmaceutically acceptable acid addition salt thereof;

or a pharmaceutically acceptable salt thereof with a base when G is $CO_2H$;

including a tautomeric form thereof.

DETAILED DESCRIPTION OF THE PREFERRED EMBODIMENTS

Compounds of the formula I can exist in tautomeric forms by virtue of the imidazole ring: the N-hydrogen atom can tautomerize from one nitrogen atom to the other of that ring. Furthermore, compounds wherein A is a group of the formula $-C(:NH)-NR^1-$, so that the side chain is $-(CH_2)_n-C(:NH)-NR^1{}_2$, where only one group $R^1$ is hydrogen, can exist in tautomeric forms. For example, if just one group $R^1$ is hydrogen, then one tautomeric form can be represented by the formula

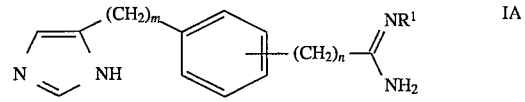

wherein m, n and $R^1$ are as defined above, except that $R^1$ is not hydrogen. The interconversion of the tautomers is catalyzed by acids. All such tautomeric forms are covered by the invention; in particular, where a compound of formula I is referred to or a compound is named according to formula I, then all such tautomeric forms of the compound are covered.

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Certain compounds of the invention are zwitterionic in nature, in particular the compounds that possess a carboxyl group in G. These compounds can form pharmaceutically acceptable salts with bases also. Examples of such salts are the sodium, potassium, calcium, aluminum, gold and silver salts, and also salts formed with pharmaceutically acceptable amines such as ammonia, alkylamines, hydroxyalkylamines, N-methylglucamine and the like.

When used herein, the following terms have the given meanings:

lower alkyl (including the alkyl portions of lower alkoxy)—represents a straight or branched, saturated hydrocarbon chain having from 1 to 6 carbon atoms, preferably from 1 to 4;

lower alkenyl (in $R^2$)—represents a straight or branched aliphatic hydrocarbon radical having at least one carbon-to-carbon double bond (preferably in conjugation with the benzene ring that the group $R^2$ substitutes) and having from 2 to 6 carbon atoms;

lower alkynyl (in $R^2$)—represents a straight or branched aliphatic hydrocarbon radical having at least one carbon-to-carbon triple bond (preferably in conjugation with the benzene ring that the group $R^2$ substitutes) and having from 2 to 6 carbon atoms;

aryl—represents a carbocyclic group having from 6 to 14 carbon atoms and having at least one benzenoid ring, with all available substitutable aromatic carbon atoms of the carbocyclic group being intended as possible points of attachment, said carbocyclic group being optionally substituted with 1 to 3 Y groups, each independently selected from halo, alkyl, hydroxy, loweralkoxy, phenoxy, amino, loweralkylamino, diloweralkylamino, and polyhaloloweralkyl. Preferred aryl groups include 1-naphthyl, 2-naphthyl and indanyl, and especially phenyl and substituted phenyl;

cycloalkyl—represents a saturated carbocyclic ring having from 3 to 8 carbon atoms, preferably 5 or 6;

halogen—represents fluorine, chlorine, bromine and iodine;

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms; e.g., 2- or 3-piperidinyl, 2- or 3-piperazinyl, 2- or 3-morpholinyl, or 2- or 3-thiomorpholinyl;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazol,2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl;

heterocyclyl-alkyl—represents a heterocyclic group defined above substituting an alkyl group; e.g., 2-(3-piperidinyl)-ethyl, (2-piperazinyl)-methyl, 3-(2-morpholinyl)-propyl, (3-thiomorpholinyl)-methyl, 2-(4-pyridyl)-ethyl, (3-pyridyl)-methyl, or (2-thienyl)-methyl.

Preferably, A is —CH$_2$—NR$^1$— or especially —C(:NH)—NR$^1$—i.e., the compounds have formula IC wherein X is H$_2$ or NH:

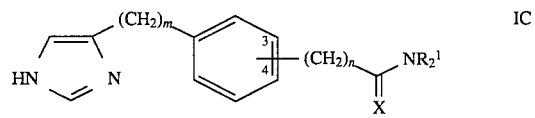

preferred compounds of the formula IC include those wherein m is 1 or 2, and n is 0, 1 or 2, more especially those of the formula

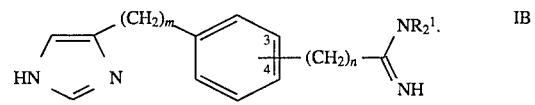

Other preferred values of A include —O—CO—N R$^1$—, —O—, and —CO—O—. In all these compounds, the groups $R^1$ are as defined above, and the side chain [—(CH$_2$)$_n$—C(=X)—NR$^1{}_2$ or —(CH$_2$)$_n$—C(=NH)—NR$^1{}_2$] is preferably at the 4-position. In compounds of formula I and especially in compounds of formulae IC and IB, one group $R^1$ is preferably selected from hydrogen, 2-phenylethyl, 4-chlorophenylmethyl, 4-methoxyphenylmethyl, 4-trifluoromethylphenylmethyl and 4-pyridylmethyl, but is especially 4-chlorophenylmethyl; any other group $R^1$ that is present is preferably a hydrogen atom or a methyl group.

Preferred compounds of the formula I include those selected from the following formulae, where the compounds bear the same numbering as in the Examples (except that the compounds in the Examples are salts, e.g., the dihydrochlorides):

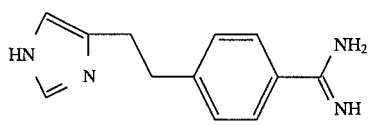 17

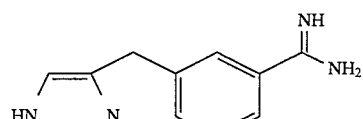 10

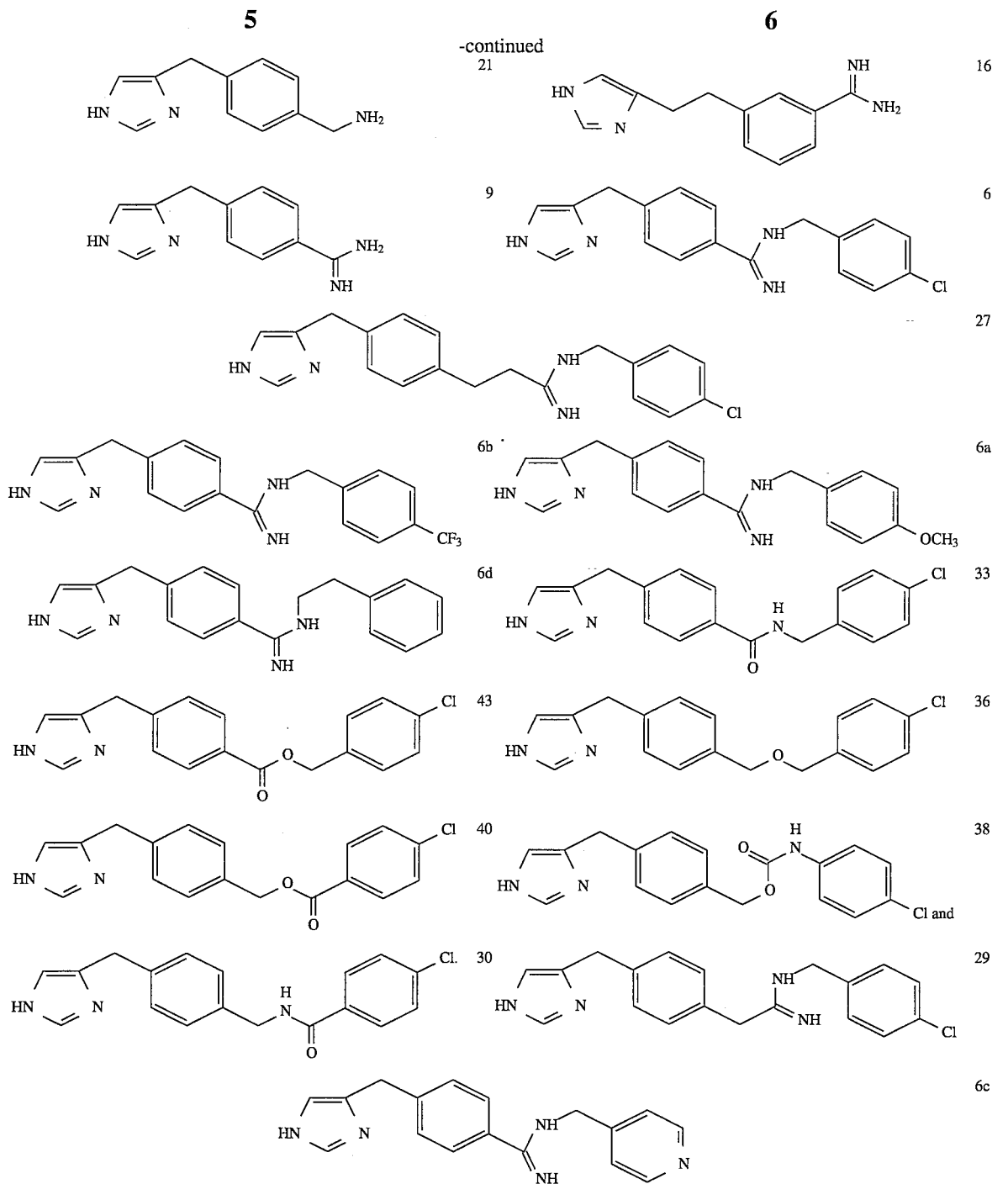

The following compounds of this invention are of special interest:

N-[(4-chlorophenyl)methyl]-4-(1H-imidazol-4-ylmethyl)benzamide;
N-[2-(4-chlorophenyl)ethyl]-4-[2-(1H-imidazol-4-yl)ethyl]benzamide;
N-phenylmethyl-4-(1H-imidazol-4-ylmethyl)benzamide;
N-[(4-chlorophenyl)methyl]-3-(1H-imidazol-4-ylmethyl)benzamide;
N-[(4-chlorophenyl)methyl]-4-[2-(1H-imidazol-4-yl)ethyl]benzamide;
N-[2-(4-chlorophenyl)ethyl]-4-(1H-imidazol-4-ylmethyl)benzamide;
(4-chlorophenyl)methyl 4-(1H-imidazol-4-ylmethyl)benzoate;
2-(4-chlorophenyl)ethyl 4-[2-(1H-imidazol-4-yl)ethyl]benzoate;
phenylmethyl 4-(1H-imidazol-4-ylmethyl)benzoate;
(4-chlorophenyl)methyl 3-(1H-imidazol-4-ylmethyl)benzoate;
(4-chlorophenyl)methyl 4-[2-(1H-imidazol-4-yl)ethyl]benzoate;
2-(4-chlorophenyl)ethyl 4-(1H-imidazol-4-ylmethyl)benzoate;
4-[[4-[[(4-chlorophenyl)methoxy]methyl]phenyl]methyl]-1H-imidazole;

4-[2-[4-[2-[(4-chlorophenyl)methoxy]ethyl]phenyl]ethyl]-1H-imidazole;

4-[[4-[(phenylmethoxy)methyl]phenyl]methyl]-1H-imidazole;

4-[[3-[[(4-chlorophenyl)methoxy]methyl]phenyl]methyl]-1H-imidazole;

4-[2-[4-[[(4-chlorophenyl)methoxy]methyl]phenyl]ethyl]-1H-imidazole;

4-[[4-[2-[(4-chlorophenyl)methoxy]ethyl]phenyl]methyl]-1H-imidazole;

[4-(1H-imidazol-4-ylmethyl)phenyl]methyl 4-chlorobenzoate;

2-[4-[2-(1H-imidazol-4-yl)ethyl]phenyl]ethyl 4-chlorobenzoate;

[4-(1H-imidazol-4-ylmethyl)phenyl]methyl benzoate;

[3-(1H-imidazol-4-ylmethyl)phenyl]methyl 4-chlorobenzoate;

2-[4-(1H-imidazol-4-ylmethyl)phenyl]ethyl 4-chlorobenzoate;

[4-[2-(1H-imidazol-4-yl)ethyl]phenyl]methyl 4-chlorobenzoate;

[4-(1H-imidazol-4-ylmethyl)phenyl]methyl N-(4-chlorophenyl)carbamate;

2-[4-[2-(1H-imidazol-4-yl)ethyl]phenyl]ethyl N-(4-chlorophenyl)carbamate;

[4-(1H-imidazol-4-ylmethyl)phenyl]methyl N-phenylcarbamate;

[3-(1H-imidazol-4-ylmethyl)phenyl]methyl N-(4-chlorophenyl)carbamate;

2-[4-(1H-imidazol-4-ylmethyl)phenyl]ethyl N-(4-chlorophenyl)carbamate;

[4-[2-(1H-imidazol-4-yl)ethyl]phenyl]methyl N-(4-chlorophenyl)carbamate;

N-[(4-chlorophenyl)methyl]-4-(1H-imidazol-4-ylmethyl)benzenecarboximidamide;

N-[(4-chlorophenyl)methyl]-4-[2-(1H-imidazol-4-yl)ethyl]benzeneethanimidamide;

N-phenylmethyl-4-(1H-imidazol-4-ylmethyl)benzenecarboximidamide;

N-[(4-chlorophenyl)methyl]-3-(1H-imidazol-4-ylmethyl)benzenecarboximidamide;

N-[(4-chlorophenyl)methyl]-4-(1H-imidazol-4-ylmethyl)benzeneethanimidamide;

N-[(4-chlorophenyl)methyl]-4-[2-(1H-imidazol-4-yl)ethyl]benzenecarboximidamide;

4-chloro-N-[[4-(1H-imidazol-4-ylmethyl)phenyl]methyl]benzamide;

4-chloro-N-[2-[4-[2-(1H-imidazol-4-yl)ethyl]phenyl]ethyl]benzamide;

N-[[4-(1H-imidazol-4-ylmethyl)phenyl]methyl]benzamide;

4-chloro-N-[[3-(1H-imidazol-4-ylmethyl)phenyl]methyl]benzamide;

4-chloro-N-[2-[4-(1H-imidazol-4-ylmethyl)phenyl]ethyl]benzamide;

4-chloro-N-[[4-[2-(1H-imidazol-4-yl)ethyl]phenyl]methyl]benzamide;

4-(1H-imidazol-4-ylmethyl)-N-[(4-methoxyphenyl)methyl]benzenecarboximidamide;

4-(1H-imidazol-4-ylmethyl)-N-[[(4-(trifluoromethyl)phenyl]methyl]benzenecarboximidamide;

4-(1H-imidazol-4-ylmethyl)-N-(4-pyridinylmethyl)benzenecarboximidamide;

4-(1H-imidazol-4-ylmethyl)-N-(2-phenylethyl)benzenecarboximidamide;

2-[4-(1H-imidazol-4-yl)ethyl]-N-(2-phenylethyl)benzeneethanimidamide;

3-(1H-imidazol-4-ylmethyl)-N-(2-phenylethyl)benzenecarboximidamide;

4-(1H-imidazol-4-ylmethyl)-N-(2-phenylethyl)benzeneethanimidamide;

2-[4-(1H-imidazol-4-yl)ethyl]-N-(2-phenylethyl)benzenecarboximidamide;

4-(1H-imidazol-4-ylmethyl)benzenecarboximidamide;

3-(1H-imidazol-4-ylmethyl)benzenecarboximidamide;

3-[2-(1H-imidazol-4-yl)ethyl]benzenecarboximidamide;

4-[2-(1H-imidazol-4-yl)ethyl]benzenecarboximidamide;

4-(1H-imidazol-4-ylmethyl)benzenemethanamine;

2-[4-(1H-imidazol-4-ylmethyl)phenyl]ethyl N-[(4-chlorophenyl)methyl]-N-methylcarbamate;

2-[4-[2-(1H-imidazol-4-yl)]ethyl]phenyl]ethyl N-[(4-chlorophenyl)methyl]-N-methylcarbamate;

2-[4-(1H-imidazol-4-ylmethyl)phenyl]ethyl N-(phenylmethyl)-N-methylcarbamate;

2-[3-(1H-imidazol-4-ylmethyl)phenyl]ethyl N-[(4-chlorophenyl)methyl]-N-methylcarbamate;

2-[4-[2-(1H-imidazol-4-yl)]ethyl]phenyl]ethyl N-[(4-chlorophenyl)methyl]carbamate;

2-[4-(1H-imidazol-4-ylmethyl)phenyl]ethyl N-[(4-chlorophenyl)methyl]carbamate;

2-[4-(1H-imidazol-4-ylmethyl)phenyl]ethyl 4-chlorobenzeneacetate;

2-[4-[2-(1H-imidazol-4-yl)ethyl]phenyl]ethyl 4-chlorobenzeneacetate;

2-[4-(1H-imidazol-4-ylmethyl)phenyl]ethyl benzeneacetate;

2-[3-(1H-imidazol-4-ylmethyl)phenyl]ethyl 4-chlorobenzeneacetate;

N'-[(4-chlorophenyl)methyl]-N-[[4-(1H-imidazol-4-ylmethyl)phenyl]methyl]-N,N'-dimethylurea;

N'-[(4-chlorophenyl)methyl]-N-[2-[4-[2-(1H-imidazol-4-yl)ethyl]phenyl]ethyl]-N,N'-dimethylurea;

N'-(phenylmethyl)-N-[[4-(1H-imidazol-4-ylmethyl)phenyl]methyl]-N,N'-dimethylurea;

N'-[(4-chlorophenyl)methyl]-N-[[3-(1H-imidazol-4-ylmethyl)phenyl]methyl]-N,N'-dimethylurea;

N'-[(4-chlorophenyl)methyl]-N-[2-[4-(1H-imidazol-4-ylmethyl)phenyl]ethyl]-N,N'-dimethylurea;

N'-[(4-chlorophenyl)methyl]-N-[[4-[2-(1H-imidazol-4-yl)ethyl]phenyl]methyl]-N,N'-dimethylurea;

4-chloro-N-[[4-(1H-imidazol-4-ylmethyl)phenyl]methyl]-N-methylbenzeneacetamide;

4-chloro-N-[2-[4-[2-(1H-imidazol-4-yl)ethyl]phenyl]ethyl]-N-methylbenzeneacetamide;

N-[[4-(1H-imidazol-4-ylmethyl)phenyl]methyl]-N-methyl-benzeneacetamide;

4-chloro-N-[[3-(1H-imidazol-4-ylmethyl)phenyl]methyl]-N-methyl-benzeneacetamide;

4-chloro-N-[[4-(1H-imidazol-4-ylmethyl)phenyl]ethyl]-N-methyl-benzeneacetamide;

4-chloro-N-[[4-[2-(1H-imidazol-4-yl)ethyl]phenyl]methyl]-N-methyl-benzeneacetamide;

(4-chlorophenyl)methyl 4-(1H-imidazol-4-ylmethyl)benzeneethanoate;

(4-chlorophenyl)methyl 4-[2-(1H-imidazol-4-yl)ethyl]benzenepropanoate;

phenylmethyl 4-(1H-imidazol-4-ylmethyl)benzeneethanoate;

(4-chlorophenyl)methyl 3-(1H-imidazol-4-ylmethyl)benzeneethanoate;

(4-chlorophenyl)methyl 4-(1H-imidazol-4-ylmethyl)benzenepropanoate;

(4-chlorophenyl)methyl 4-[2-(1H-imidazol-4-yl)ethyl]benzeneethanoate;

4-[[4-[[(3-chlorophenyl)methoxy]methyl]phenyl]methyl]-1H-imidazole;

N-[(4-chlorophenyl)methyl]-[4-(1H-imidazol-4-ylmethyl)-N-methyl-benzeneethanimidamide;

N-[(4-chlorophenyl)methyl]-4-[2-(1H-imidazol-4-yl)ethyl]-N-methyl-benzenepropanimidamide;

N-(phenylmethyl)-[4-(1H-imidazol-4-ylmethyl)-N-methyl-benzeneethanimidamide;

N-[(4-chlorophenyl)methyl]-[3-(1H-imidazol-4-ylmethyl)-N-methyl-benzeneethanimidamide;

N-[(4-chlorophenyl)methyl]-[4-(1H-imidazol-4-ylmethyl)-N-methyl-benzenepropanimidamide;

N-[(4-chlorophenyl)methyl]-4-[2-(1H-imidazol-4-yl)ethyl]-N-methyl-benzeneethanimidamide;

N-[(4-chlorophenyl)methyl]-4-[2-(1H-imidazol-4-yl)ethyl]benzenepropanimidamide;

N-(phenylmethyl)-4-(1H-imidazol-4-ylmethyl)benzeneethanimidamide;

N-[(4-chlorophenyl)methyl]-3-(1H-imidazol-4-ylmethyl)benzeneethanimidamide; and

N-[(4-chlorophenyl)methyl]-4-(1H-imidazol-4-ylmethyl)benzenepropanimidamide.

Compounds of this invention are antagonists of the $H_3$ receptor. As such, they may be useful for the treatment of various allergic, inflammatory, GI-tract, or cardiovascular diseases. In addition, they possess CNS activity; they may be useful as sleep regulators, anticonvulsants, cognition enhancers, anti-depressants, regulators of hypothalamo-hypophyseal secretions, and the like.

A further feature of the invention therefore is pharmaceutical compositions containing as active ingredient a compound of the formula I defined above (or salt or tautomer), especially a compound of the formula IC, together with a pharmaceutical carrier or excipient.

Further features of the invention are methods for treating inflammation, allergy, diseases of the GI-tract, cardiovascular disease, or disturbances of the central nervous system, which comprise administering to a patient suffering from the corresponding disease an effective amount of a compound of the formula I defined above (or salt or tautomer).

Preparation of Final Products

Compounds of the formula I can be prepared by standard methods. Typical methods appropriate for the preparation of the compounds of the formula I are illustrated below, wherein the radicals, m and n are as defined above (unless otherwise stated) and $\phi$ represents a phenyl group; for convenience, the group $R^2$ has been omitted from the reaction schemes, but its absence does not affect the operability of the chemical reactions. The particular process chosen should not cause significant decomposition elsewhere in the molecule; for example, removal of a protecting group by hydrogenolysis should not cause the loss of an essential phenylmethyl group. The first processes A through E illustrate methods for the preparation of compounds of the formula IC.

A. For the preparation of a compound of formula IC wherein X is NH, reduction of an amidoxime of the formula:

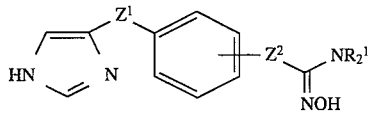

II (or an acid addition salt thereof) wherein $Z^1$ is a group $(CH_2)_m$, or a dehydro derivative thereof when m is 2 or 3, and $Z^2$ is a group $(CH_2)_n$, or a dehydro derivative thereof when n is 2 or 3. The reduction can be effected for example by means of catalytic hydrogenation in an inert solvent, e.g., over $Rh/Al_2O_3$ or Pd/C, but especially over Raney nickel; the solvent is preferably a lower alkanol. (A dehydro derivative of a compound of formula II wherein m and/or n is 2 or 3 will have a double bond in the carbon chain between the imidazole ring and the phenyl ring or between the phenyl ring and the group $C(:NOH)NR^1_2$; this double bond will be reduced in the same step as the reduction of the group $C(:NOH)NR^1_2$.)

B. Removal of a protecting group from a compound of the formula:

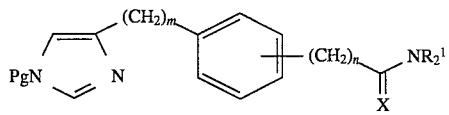

III wherein Pg is a protecting group. The protecting group is preferably one that can be removed by hydrolysis or hydrogenolysis; it can for example be a trityl group $(C_6H_5)_3C—$, which is preferably removed by hydrolysis in an aqueous organic solvent. The hydrolysis can for example be effected by means of mineral acid in an aqueous water-miscible organic solvent such as a lower alkanol, especially methanol or ethanol. Other protecting groups that can be used (and their method of removal) include t-Bu—O.CO— [often abbreviated to t-BOC] (which can be removed with acid, or with hydrazine, ammonia and a lower alkanol, e.g., methanol or ethanol), (2-triloweralkylsilyl)ethoxymethyl groups, especially $Me_3Si.(CH_2)_2.O.CH_2—$ [often abbreviated to SEM] (which can be removed with acid or fluoride ion), and disubstituted aminosulfonyl, especially $Me_2N.SO_2$ (which can be removed with acid or base).

C. For the preparation of a compound of formula IC wherein X is NH, reaction of an imidate salt containing a cation of the formula

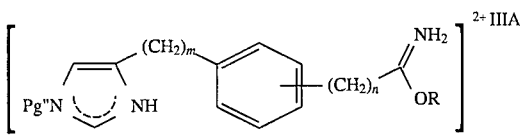

wherein m and n are as defined above, Pg" is a hydrogen atom or preferably a protecting group (such as $Me_2N.SO_2$), and R is a lower alkyl group, especially a methyl or ethyl group, with an amine of the formula $NHR^1{}_2$, wherein the groups $R^1$, which may be the same or different, are as defined above, according to the general method disclosed by Pinner in "Die Imidoäther und ihre Derivate", R. Oppenheim, Berlin, 1892 (when Pg" is preferably a hydrogen atom), or the adaptation disclosed by Dox, *Org. Synth., Coll.* Vol. 1, 5 (1941). The anion associated with the cation of the formula IIIA may for example be methosulfate or fluoroborate (as disclosed by Weintraub et al., *J. Org. Chem.*, Vol. 33 no. 4 (April 1968), pp. 1679–1681), but is most preferably a halide (e.g., chloride).

D. Reaction of a nitrile of the formula IV:

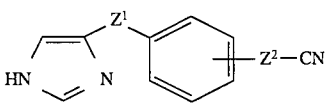

with an ammonium salt, to yield a compound of the formula I wherein X is NH, or reduction of the nitrile of the formula IV to yield a compound of the formula IC wherein X is $H_2$. These processes provide a compound of the formula IC wherein both groups $R^1$ are hydrogen. Preferred reducing agents include lithium aluminum hydride (when $Z^1$ and $Z^2$ do not contain double bonds), or catalytic hydrogenation, e.g., with Raney nickel and chloroplatinic acid (especially when $Z^1$ and $Z^2$ do contain double bonds).

E. For the preparation of a compound of formula IC wherein X is $H_2$, reaction of an aldehyde of the formula

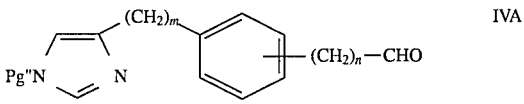

wherein Pg" is a hydrogen atom or a protecting group, with an amine of the formula $NHR^1{}_2$, in the presence of a reducing agent and of an inert organic solvent. The reducing agent may for example be Raney nickel or sodium cyanoborohydride. Any protecting group Pg" that is present after the reduction can be removed, for example as described above under Process B.

In all of these processes, reactive or functional groups that might become modified during the process (or might even cause large-scale decomposition of the compounds) should be protected with protecting groups that can be readily removed when the process has been carried out. (Such groups may include, but are not restricted to, for example, a hydroxy group OH in G.) Details of such groups and of their removal are well known in the art and are given in standard textbooks, for example "Protective Groups in Organic Synthesis", by Greene and Wuts (2nd Edition, John Wiley & Sons, Inc., 1991).

Preparation of Starting Materials and Intermediates

Starting materials for processes A, B, C, D and E can be prepared by the methods discussed below, wherein: Y represents a group convertible into —$(CH_2)_n$.$CX.NR_1$, e.g., CN or a group convertible into $Z^2$—CN; M and $y^1$ are as defined in Table 1 below; and $Z^1$, $Z^2$, Pg and Pg" are as hereinabove defined; except that, when $Y^1$ represents a divalent group, then $Z^1$, to compensate, lacks a hydrogen atom from the carbon atom bonded to $Y^1$; and, when $Y^1$ contains a carbon atom, then $Z^1$ contains one carbon atom fewer.

Main preliminary reaction stage:

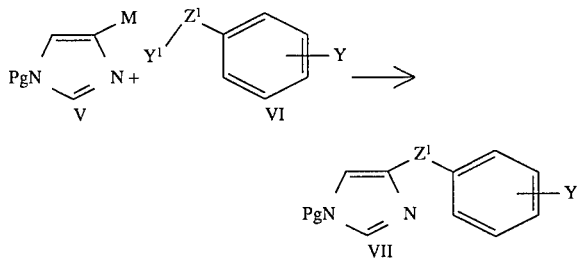

Reaction conditions (for both steps, where there is more than one) are given in the following Table, wherein OTs stands for toluene-4-sulfonyloxy, TCDI stands for thiocarbonyldiimidazole, and AIBN stands for azoisobutylnitrile.

TABLE 1

| M | $Y^1$ | Solvent | Temperature | Comments |
|---|---|---|---|---|
| MgBr, CuI | I, Br, OTs or THF | $CH_2Cl_2$ reflux | 0° C. to | |
| MgBr | =O | $CH_2Cl_2$ or THF | 0° C. to reflux | Reduction of hydroxy group in second step can be effected with TCDI, $BU_3SnH$ and AIBN in benzene/ toluene from 0° to reflux |
| MgBr, CuI | COCl, $CO_2$ alkyl | $CH_2Cl_2$ or THF | 0° C. to reflux | Reduction of carbonyl group in second step can be effected under Wolff-Kishner conditions, or with an alkanedithiol (to form a thioketal) and Raney nickel under reflux |

Values of Y (and $Z^2$) in Intermediates

The group Y representing CN or a group convertible into $Z^2$—CN can also be represented by $Z^2Y^2$ wherein $Z^2$ is as hereinabove defined and $Y^2$ is a group convertible into CN; except that, when $Y^2$ represents a divalent group, then $Z^2$, to compensate, lacks a hydrogen atom from the carbon atom bonded to $y^2$. When n in the compound of formula IC is to be 0 (i.e., when $Z^2$ is simply a bond), Y is preferably CN. When n is to be 1, 2 or 3, the group Y can be provided by the following reaction schemes, wherein the radicals are as defined above, and φ represents a phenyl group:

I) For n=1, Y is preferably —$CH(OR)_2$, wherein R is lower alkyl, preferably Me or Et, or the two groups R together form an ethylene or a trimethylene group:

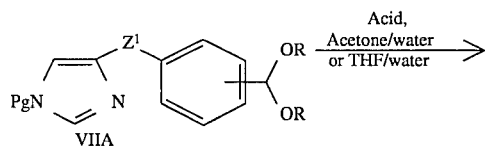

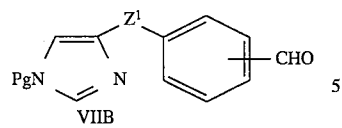

This yields an aldehyde of the formula VIIB having Y=CHO; it can be converted into a compound of the formula VII wherein Y=CN by reaction with tosylmethylisocyanide and t-BuOK and then methanol, or with KCN and

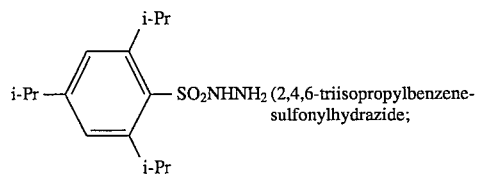

II) For n=2, Y again is preferably —CH(OR)$_2$, which can be converted as above and then through —CH=CH—CN into —CH$_2$CH$_2$—CN:

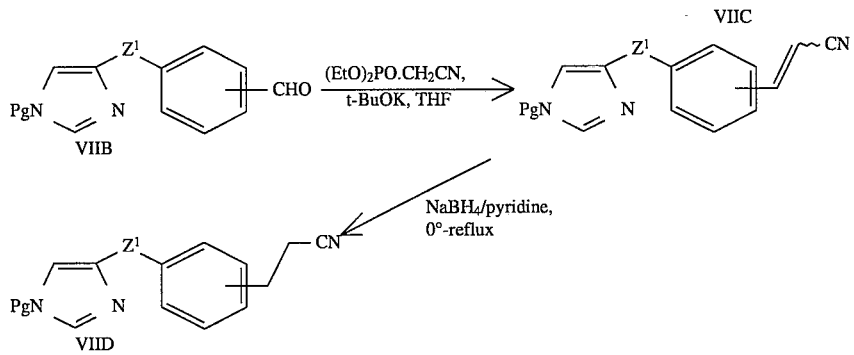

III) For n=3, Y is preferably —CH(OR)$_2$, which can be converted through —CHO, —CH$_2$—CHO and —CH$_2$—CH=CH—CN into —CH$_2$CH$_2$CH$_2$—CN, analogously to methods given above:

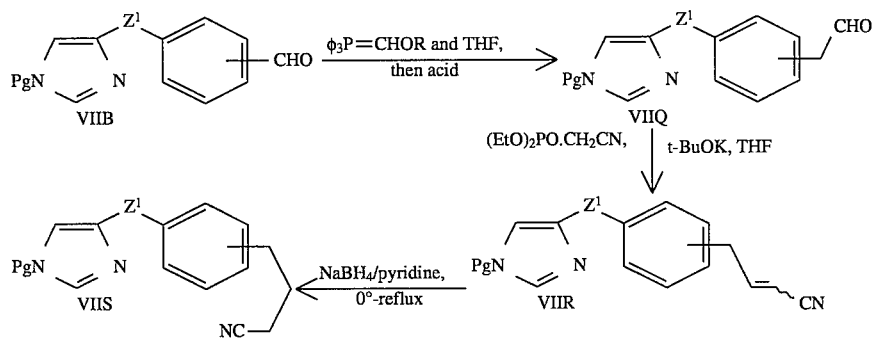

Values of $Z^1$ in Intermediates

Compounds of the formula VII can be prepared by the following schemes, wherein the radicals are as defined above, φ represents a phenyl group, and Q represents a hydrocarbyl group, preferably a lower alkyl group, especially methyl or ethyl:

i) For m=1, a metal derivative of an N-protected imidazole of the formula V (wherein M is e.g. MgBr) can be reacted with a Y-substituted-benzaldehyde of the formula VIA, and the resulting substituted benzyl alcohol of the formula VIIE can be reduced, for example as indicated in the following scheme:

Compounds of the formula V can be prepared from the corresponding iodide by the methods of the references given in *J. Org. Chem.* 1991, 56, 5739–5740.

Aldehydes for use in process E above are for example compounds of the formulae VII and VIIQ in paragraph III) above wherein $Z^1$ is a group (CH$_2$)$_m$, or can be prepared therefrom by lengthening of the aldehyde side-chain.

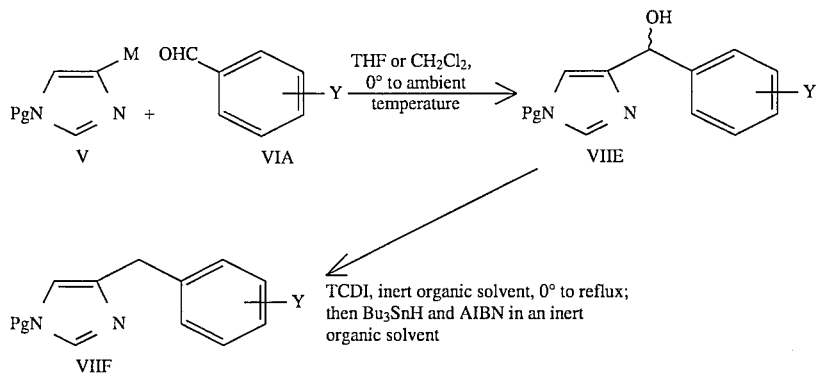
ii) For m=2, one of the following schemes can be used:
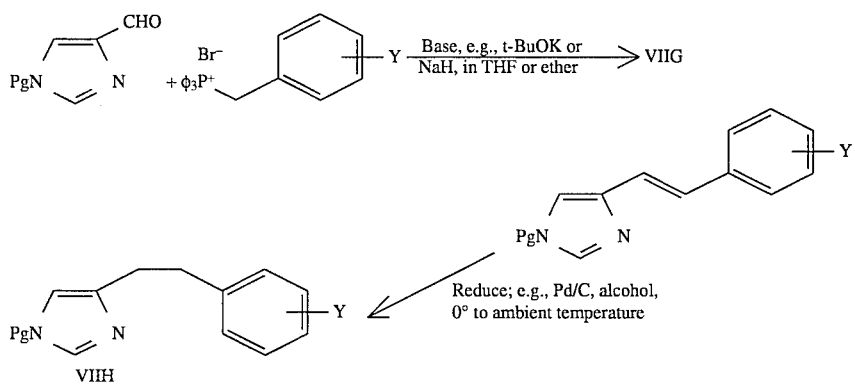
a)
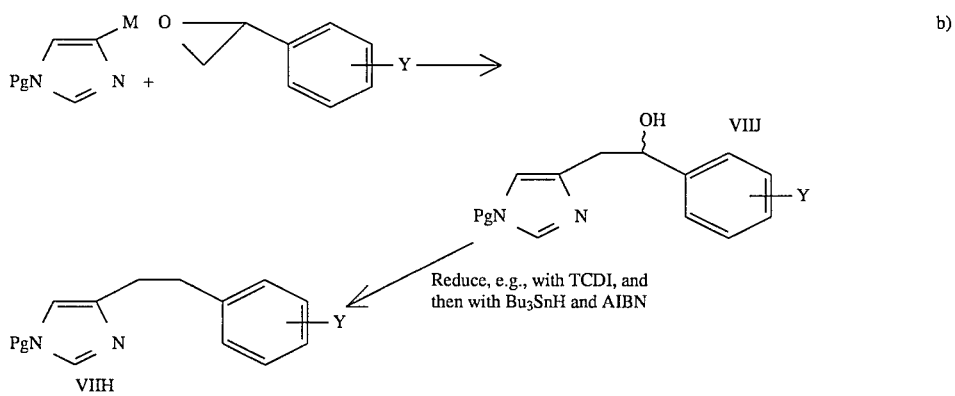
b)
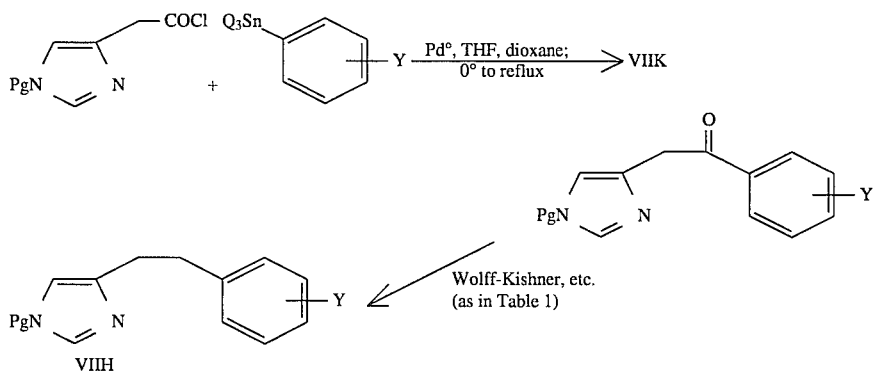
c)
iii) For m=3, one of the following schemes can be used:

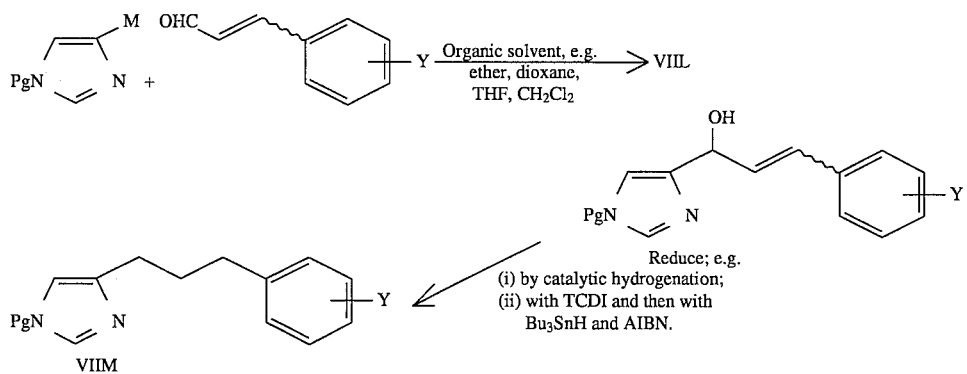

a)

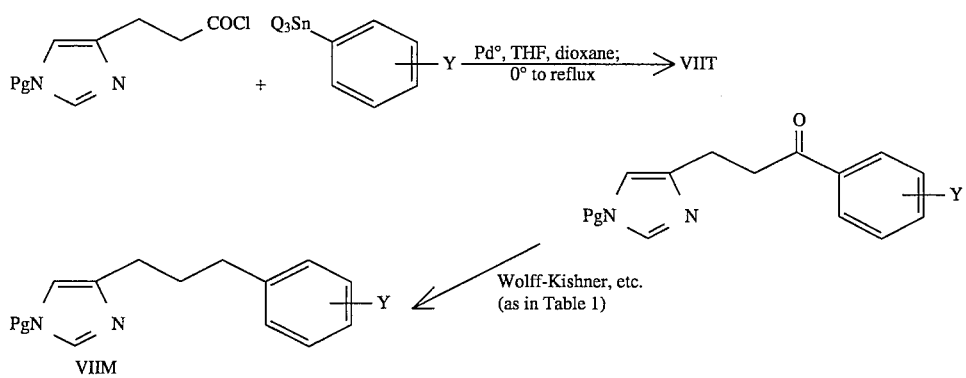

b)

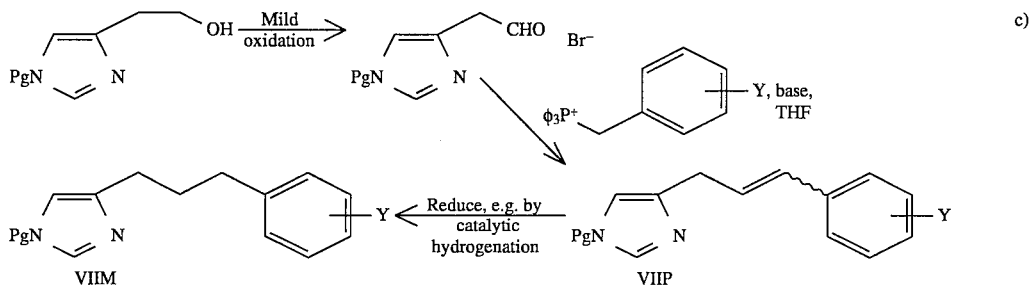

c)

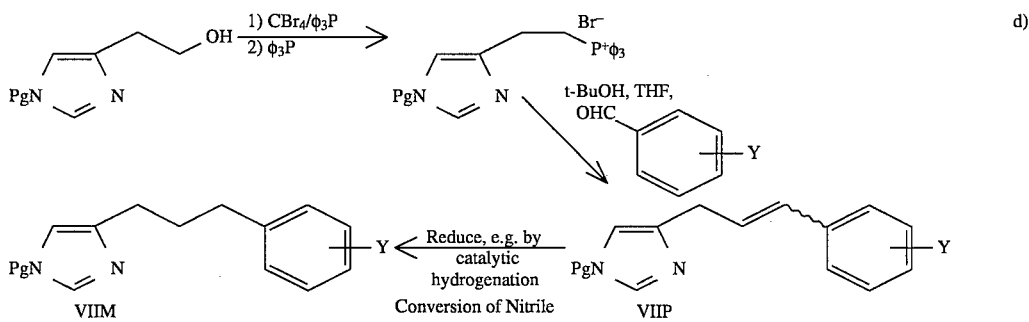

d)

The compound of the formula VII (designated VIIA through VIIS above, but VII' or VII" in the following schemes) wherein Y represents CN or a group convertible into $Z^2$—CN can then be converted into the starting material for Process A, B, C or D by the following processes I, II, or III, respectively:

I. Conversion of a compound of the formula VII' into an amidoxime of the formula IIA:

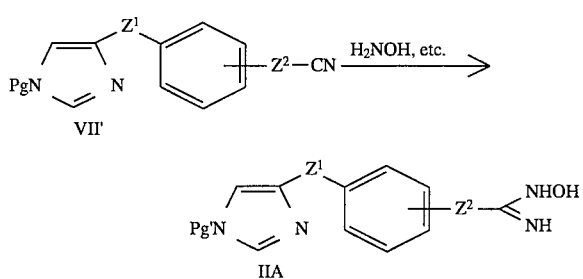

This reaction can be carried out with a hydroxylamine salt, e.g., the hydrochloride, in the presence of a base such as potassium hydroxide in an inert organic solvent such as ethanol at elevated temperature, e.g., under reflux. The group Pg' represents a protecting group (if that group is stable to the reaction conditions) or a hydrogen atom (if the protecting group is displaced under the reaction conditions, as for example a trityl group is).

II. Conversion of a compound of the formula VII' into an amidine of the formula IIB:

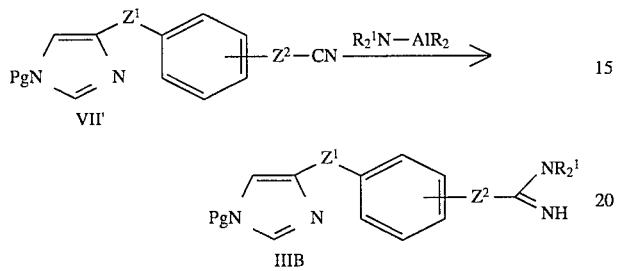

This reaction can be carried out in the presence of an inert organic solvent, preferably an aromatic hydrocarbon such a benzene or toluene, at elevated temperature, e.g., 50° to reflux, and under an inert atmosphere. The dialkylaluminoamine of the formula $R^1_2N$—AlR can be generated by reaction of a trialkylaluminum $R^3Al$ with an amine $R^1_2NH$ (or its hydrochloride) in the solvent in which the main reaction will be carried out, under an inert atmosphere.

III. Conversion of a compound of the formula VII" into an imidate salt containing a cation of the formula IIIA:

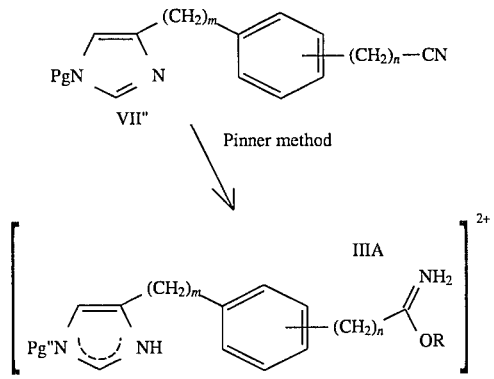

This reaction is carried out by passing a stream of dry HCl through a solution of the nitrile in a lower alkanol, preferably ethanol or methanol.

For process A, C, D or E, any remaining protecting group (designated Pg, Pg' or Pg") can be removed, for example as set out under Process B above.

PREPARATION OF FURTHER COMPOUNDS

Compounds of the formula I wherein A is selected from —O—CO—$NR^1$—, —O—CO—, —$NR^1$—CO—$NR^1$—, —$NR^1$—CO—, —O—, —CO—$NR^1$—, —CO—O—, can be prepared by a process in which the left-hand part of the molecule represented by

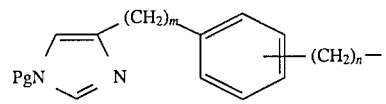

is coupled to a compound providing the remainder of the molecule, including the group $R^1$. Specific examples of processes for the preparation of such compounds follow:

1. For the preparation of a compound of the formula I wherein A is —O—CO—$NR^1$—, reaction of a hydroxy compound with an isocyanate:

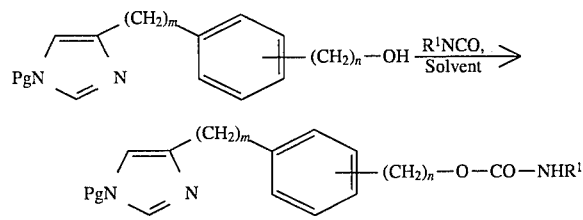

The resulting compound can then if desired be reacted with an alkylating agent to introduce another group $R^1$ on to the nitrogen atom in the side chain.

The hydrogen compound can be prepared by reaction of a cyanide of the formula VII' with an alkanol and an alkoxide (e.g., sodium or potassium methoxide or ethoxide) and then with the alkanol and an acid to form an ester, which can then be reduced with a hydride reducing agent such as DiBALH and lithium aluminum hydride. However, it should be noted that the number of carbon atoms in the group $Z^2$ in the compound of the formula VII' will increase by 1 in this process.

2. For the preparation of a compound of the formula I wherein A is —$NR^1$—CO—$NR^1$—, reaction of a amino compound with an isocyanate:

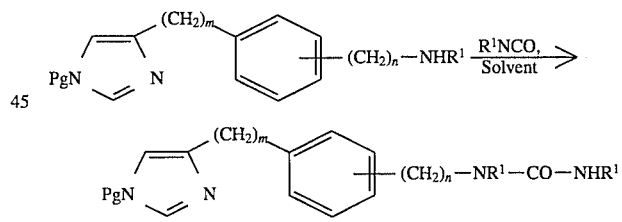

The resulting compound can then if desired be reacted with an alkylating agent to introduce another group $R^1$ on to the N—(H) atom in the side chain. Any resulting mixture of products can then be resolved by standard methods such as chromatography.

The amino compound can be prepared for example by reduction of a cyanide of the formula VI' with a hydride reducing agent such as DiBALH or lithium aluminum hydride, or by catalytic hydrogenation with e.g. Raney nickel or palladium on carbon.

3. For the preparation of a compound of the formula I wherein A is —O—CO— or —$NR^1$—CO—, reaction of a hydroxy or amino compound (as given in process 1 or 2 above) with a reactive derivative of an acid, especially the acid chloride:

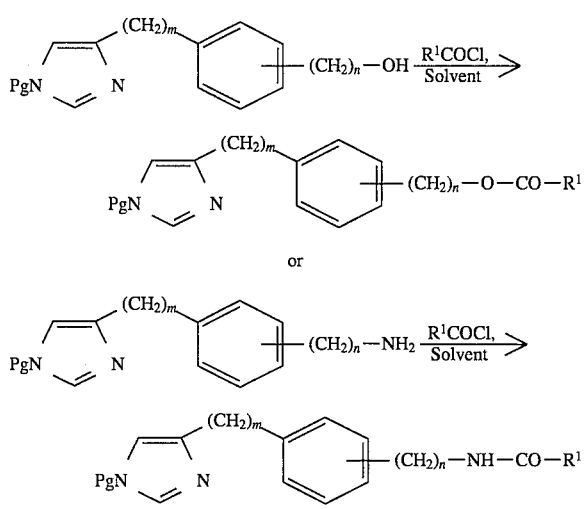

4. For the preparation of a compound of the formula I wherein A is —O—, reaction of a hydroxy compound with a halide (according to the Williamson synthesis of ethers):

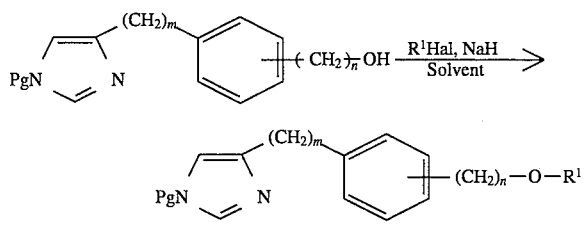

5. For the preparation of a compound of the formula I wherein A is —CO—NR$^1$—, reaction of an ester with an dialkylaluminoamine, preferably one of the formula Me$_2$AlNR$^1$$_2$:

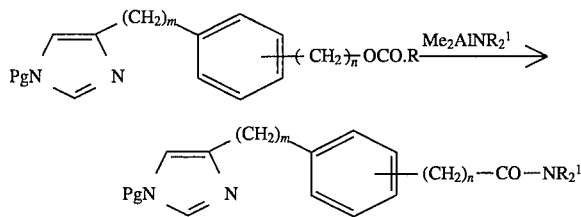

6. For the preparation of a compound of the formula I wherein A is —CO—O—, reaction of a reactive derivative of an acid, preferably a chloride, with an alcohol R$^1$OH in the presence of a base, preferably an organic base such as a tertiary amine (e.g., pyridine or triethylamine):

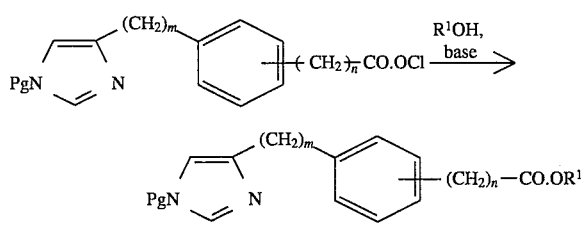

The acid chloride can be prepared by reaction of the corresponding acid with SOCl$_2$, and this acid can be prepared by hydrolysis of a cyanide of the formula VII' with an alkanol and an alkoxide (e.g., sodium or potassium methoxide or ethoxide).

All these reactions can be carried out by methods that are well known and/or disclosed in the literature. Further details are given in the Examples.

EXAMPLES

The following Examples illustrate but do not in any way limit the present invention:

Example 1

N-[(4-Chlorophenyl)methyl]-4-[(1H-imidazol-4-yl)methyl]benzene methanimidamide (as dihydrochloride)

Part A.

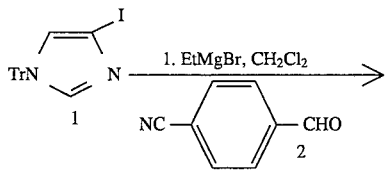

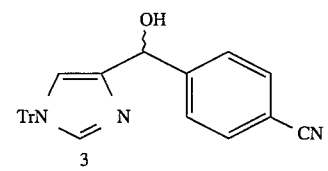

A solution of ethyl magnesium bromide in ether (8.4 mL of a 3M solution) was added to a solution of iodide 1 (synthesized according to the references given in J. Organic Chem. 1991, 56, 5739–5740; 10 g, 22.9 mmol) in CH$_2$Cl$_2$ (90 mL) at room temperature under a nitrogen atmosphere. The reaction was stirred at room temperature for 30 minutes and a solution of aldehyde 2 (3.0 g, 22.9 mmol) in CH$_2$Cl$_2$ (15 mL) was then added. The reaction was stirred overnight (about 18 hours) and then quenched by the addition of half-saturated NH$_4$Cl (100 mL). The organic layer was separated and the aqueous layer was extracted with additional CH$_2$Cl$_2$ (100 mL). The combined organic layers were dried (MgSO$_4$), filtered, and concentrated to give a white solid (11 g), which was triturated with CH$_2$Cl$_2$ (100 mL) to yield 5.5 g of the desired material. Repetition of this procedure gave an additional 1.55 g of product. The filtrate was concentrated and the residue subjected to column chromatography (85:15 ether:acetone) which yielded a further 1.77 g of the desired material. Total yield 8.82 g (87%).

Part B.

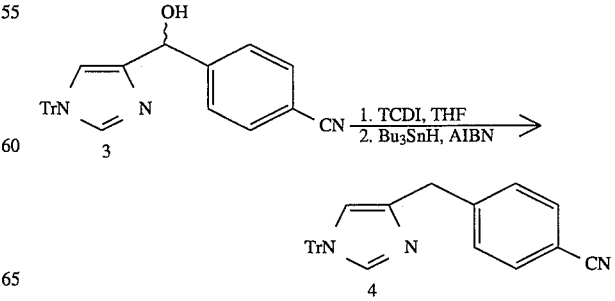

A suspension of 3 (6.5 g, 14.7 mmol) and thiocarbonyldiimidazole (TCDI, 3.94 g, 22.1 mmol) was heated to reflux in THF (150 mL) under a nitrogen atmosphere. After 2 hours, additional thiocarbonyldiimidazole (1 g) was added and the reaction stirred overnight at room temperature. The reaction mixture was concentrated and the dark residue was dissolved in CH₂Cl₂ and washed with half-saturated NH₄Cl. The organic layer was separated, and the aqueous layer was extracted with additional CH₂Cl₂ (2×75 mL). The combined organic layers were washed successively with water and brine, and dried with MgSO₄. Filtration and concentration gave a dark solid that was purified on a flash column (70:30 hexane:ethyl acetate) to give the thioimidazolide (7 g, 86%). A solution of the thioimidazolide (10 g, 18.15 mmol) and AIBN (azoisobutylnitrile) (0.45 g) in dry toluene (200 mL) was slowly added to a solution of n-Bu₃SnH (11.1 g, 38.1 mmol) in refluxing dry toluene (200 mL) over about 2 hours under a nitrogen atmosphere. Additional AIBN (0.2 g) and n-Bu₃SnH (3 g) were added, and the reaction was stirred overnight at reflux. It was then cooled to room temperature and washed with 0.1N HCl, saturated aqueous sodium bicarbonate and water, and dried (MgSO₄). Concentration gave a crude solid which was purified on a flash column (85:15 hexane:isopropanol) to give 6.5 g (85%) of 4 as a white solid.
Part C.

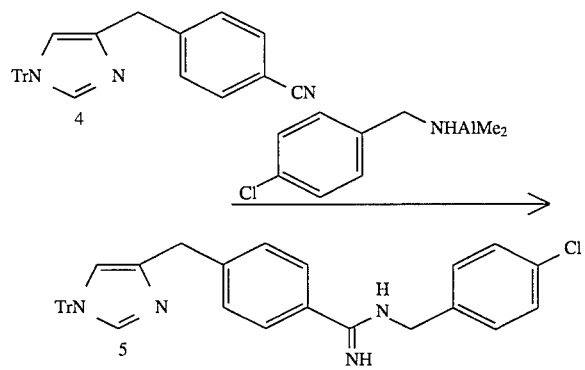

A solution of 4-chlorobenzyl amine (0.16 g, 1.1 mmol) in toluene (3 mL) was added dropwise to a solution of Me₃Al (0.55 mL of a 2M solution in toluene, 1.1 mmol) in toluene (5 mL) at room temperature and under a nitrogen atmosphere. After 45 minutes at room temperature, 4 (0.213 g, 0.5 mmol) in toluene (3 mL) was added and the reaction was heated to 80° C. overnight. An additional two equivalents of the aluminum reagent (from Me₃Al and 4-chlorobenzyl amine) was added and the reaction stirred for 2 hours at 100° C. The reaction was then cooled to room temperature and quenched by the addition of saturated aqueous sodium sulfate. When gas evolution ceased, solid sodium sulfate was added. The mixture was filtered, concentrated, and purified on a flash column (100 g SiO₂, 92:8 CH₂Cl₂:MeOH/NH₃). A white solid was obtained (230 mg, 81%).
Part D.

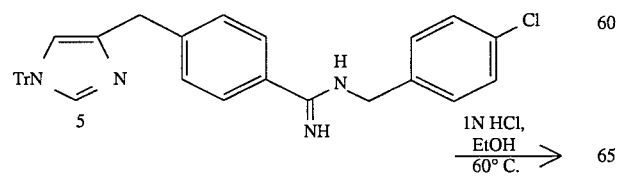

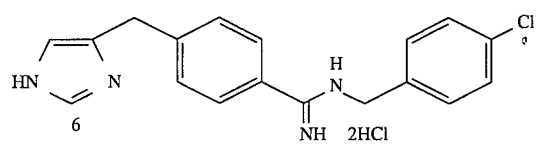

1N HCl (20 mL) was added to a solution of 5 (0.51 g, 0.9 mmol) in ethanol (25 mL) and the reaction heated to 60° C. for 2 hours. After cooling to room temperature, water (50 mL) was added and the solid that precipitated was removed by filtration. The aqueous layer was washed with ether and concentrated in vacuo. A white glassy solid, 6, was obtained (0.24 g, 67%).

Example 2

In a similar manner to that of Example 1, the following compounds were obtained:

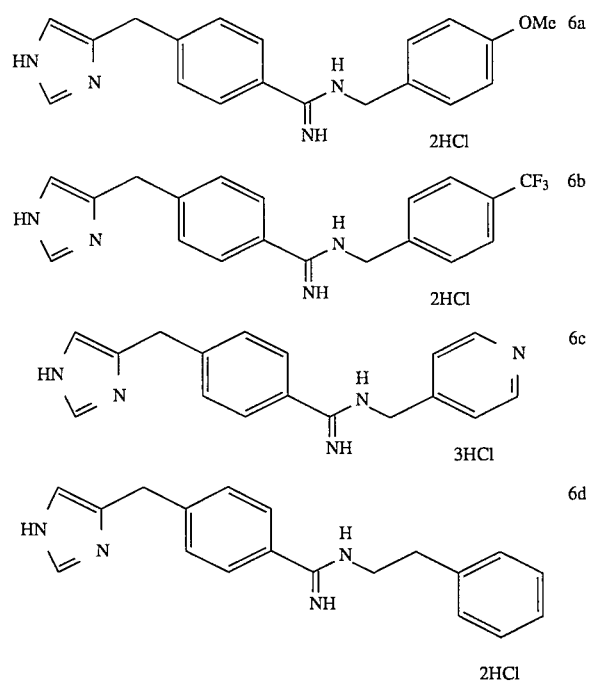

6a: N-[(4-Methoxyphenyl)methyl]-4-[(1H-imidazol-4-yl)methyl]benzene methanimidamide (as dihydrochloride);

6b: N-[(4-trifluoromethylphenyl)methyl]-4-[(1H-imidazol-4-yl)methyl]benzene methanimidamide (as dihydrochloride);

6c: N-[(4-Pyridyl)methyl]-4-[(1H-imidazol-4-yl)methyl]benzene methanimidamide (as dihydrochloride);

6d: N-(2-Phenylethyl)-4-[(1H-imidazol-4-yl)methyl]benzene methanimidamide (as dihydrochloride):

Example 3

4-[(1H-Imidazol-4-yl)methyl]benzene methanimidamide (as dihydrochloride)

Part A.

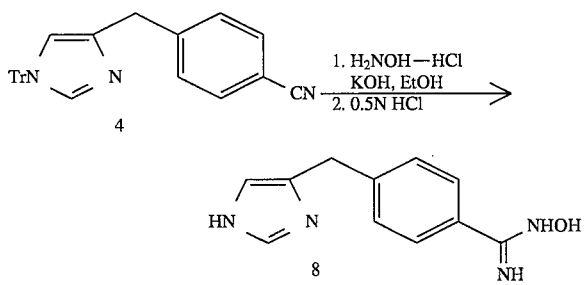

Hydroxylamine hydrochloride (0.90 g, 13 mmol) and potassium hydroxide (0.73 g, 13 mmol) were stirred for 5 minutes in absolute ethanol at room temperature. Compound 4 (0.55 g, 1.3 mmol) in absolute ethanol (25 mL) was added and the reaction heated to reflux for three hours. It was then cooled to room temperature, filtered, and concentrated to give a white solid. This solid was dissolved in 0.5N HCl and heated to 50° C. for one hour. The mixture was cooled, filtered, and washed with ether. The aqueous layer was concentrated and the residue applied to a flash column (85:15 $CH_2Cl_2$: $MeOH/NH_3$). Compound 8 was obtained as a white solid (0.125 g, 44%).

Part B.

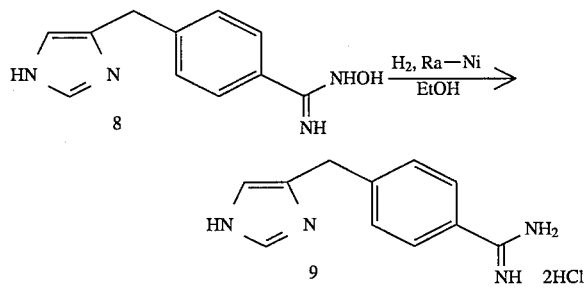

A solution of 8 (0.12 g, 0.56 mmol) and Raney-Nickel (about 0.1 g wet) were hydrogenated on a Parr shaker under 4.4 kg.cm.$^{-2}$ $H_2$ pressure (63 psi $H_2$) at room temperature overnight. The heterogeneous mixture was filtered through Celite, and the filter cake washed with additional ethanol. The ethanol was removed on the rotary evaporator, and the residue purified by HPLC (RCM 25×10 silica gel column eluted with acetonitrile:water:conc. HCl 1600 mL:400 mL:0.5 mL at 3 mL/min.). Compound 9 (0.123 g, 81%) was obtained as a glass.

Example 4

3-[(1H-Imidazol-4-yl)methyl]benzene methanimidamide (as dihydrochloride)

In the same manner as that used to prepare compound 9, compound 10 was prepared.

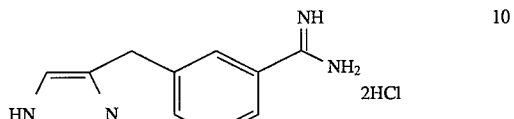

Example 5

3-[(1H-Imidazol-4-yl)ethyl]benzene methanimidamide (as dihydrochloride)

Part A.

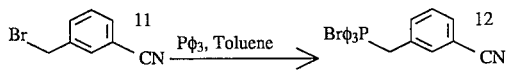

The nitrile 11 (9.8 g, 0.05 mole) and triphenylphosphine (14.4 g, 0.055 mole) were combined in toluene (100 mL) and heated to reflux under a nitrogen atmosphere for 8 hours. A white precipitate formed. The reaction was cooled, and the solid was collected by filtration and washed with toluene (150 mL), and dried under vacuum. A white solid was obtained (19.7 g, 86%) and used without further purification in the next step.

Part B.

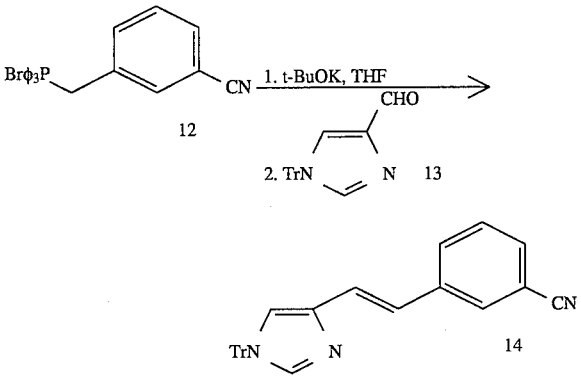

A solution of potassium t-butoxide in THF (16.3 mL of a 1M solution) was added dropwise to a suspension of the phosphonium salt 12 (7.45 g, 16.3 mmol) in dry THF (45 mL) under a nitrogen atmosphere at room temperature. The orange suspension was stirred for three minutes and a solution of the aldehyde 13 (5 g, 14.8 mmol) [prepared according to Bernabé and Burger, *J. Med. Chem.*, 14 (1971) 883–885]in dry THF (45 mL) was added. After 3.5 hours at room temperature, the reaction was diluted with ether and filtered through Celite. The Celite was washed with additional ether. The organic layer was dried ($MgSO_4$) and concentrated to give a solid that was purified on a flash column ($SiO_2$, 1:1 hexane:ethyl acetate) to give 5.03 g (78%) of 14 as a white solid.

Part C.

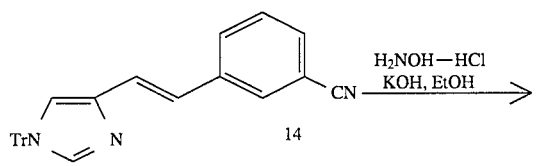

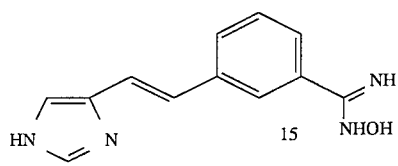

Hydroxylamine hydrochloride (8 g, 115 mmol) and potassium hydroxide (6.8 g, 121 mmol) were combined in ethanol (100 mL) and heated to 50° C. for 10 minutes. A solution of 14 (5.03 g, 11.5 mmol) in ethanol (100 mL) was added and the reaction heated to reflux for 2 hours. It was cooled, filtered and concentrated. The solid that was obtained was dissolved in 1N HCl (80 mL) and heated to 60° C. After 1.5 hours the reaction mixture was filtered and the aqueous layer was washed with ether and concentrated. The residue was dissolved in methanol/$NH_3$ and stirred for twenty minutes. The solvent was removed and the residue dissolved in ethyl acetate and methylene chloride (80:20) and washed with water. The aqueous layer was extracted again and the combined organic layers were dried ($MgSO_4$), filtered, and concentrated to give 2.5 g (94%) of 15 as a white solid.

Part D.

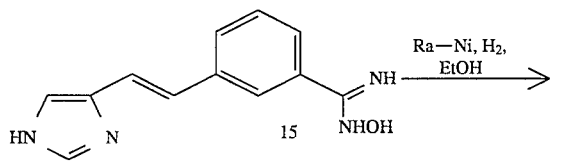

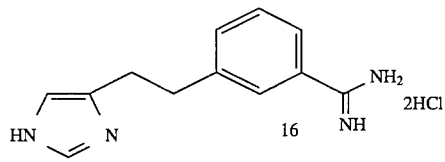

Raney nickel (about 0.5 g wet) and compound 15 (0.46 g, 2 mmol) in ethanol (50 mL) were combined in a Parr bottle and hydrogenated under 4.2 kg.cm.$^{-2}$ $H_2$ pressure (60 psi $H_2$) 60 psi $H_2$. After 20 hours, the mixture was filtered and the residue was washed with additional ethanol. Upon concentration, an amber gum was obtained which was purified by HPLC (RCM 25×10, $SiO_2$, acetonitrile:water::conc. HCl 1600 mL:400:0.5, 3 mL/min, 254 nm). Compound 16 was obtained as a glass (0.31 g, 54%).

Example 6

4-[(1H-Imidazol-4-yl)ethyl]benzene methanimidamide (as dihydrochloride)

In a manner similar to that used to prepare compound 16, compound 17 was prepared.

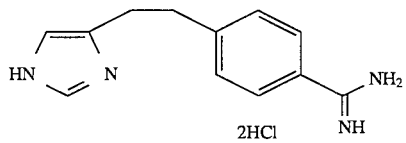

Example 7

4-[(1H-Imidazol-4-yl)methyl]benzenemethanamine (as dihydrochloride)

Part A.

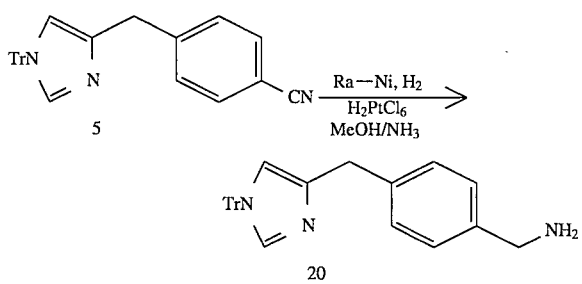

Compound 4 (1.53 g, 3.6 mmol) was combined with Raney-Nickel (about 1 g), methanol saturated with ammonia (50 mL), and chloroplatinic acid (0.8 mL of a solution of 1.0 g of the acid in 10 mL of water) in a Parr bottle and shaken under 4.2 kg.cm.$^{-2}$ $H_2$ pressure (60 psi $H_2$) for 24 hours. The reaction was filtered through Celite and concentrated on the rotary evaporator. The crude material was purified on a flash column (200 g $SiO_2$; 95:5 $CH_2Cl_2$: MeOH/$NH_3$) to give 1.31 g (85%) of 20 as a white solid.

Part B.

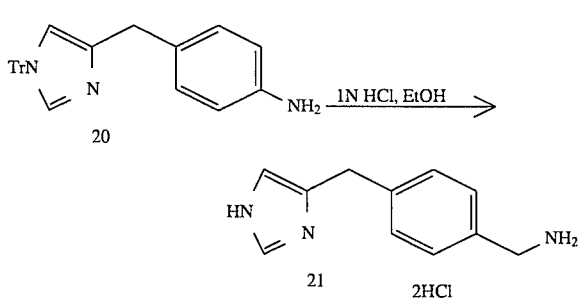

To a solution of 20 (1.31 g, 3.1 mmol) in absolute ethanol (30 mL) was added 1N HCl (20 mL) and the heterogeneous mixture heated to 70° C. for 2 hours. The reaction was cooled, filtered, and concentrated. Water (50 mL) was added and the solution washed with ether. The aqueous layer was concentrated to give a white solid (0.8 g, 99%).

Example 8

N-[(4-Chlorophenyl)methyl]-4-[(1H-imidazol-4-yl)methyl]benzene propanimidamide (as dihydrochloride)

Part A.

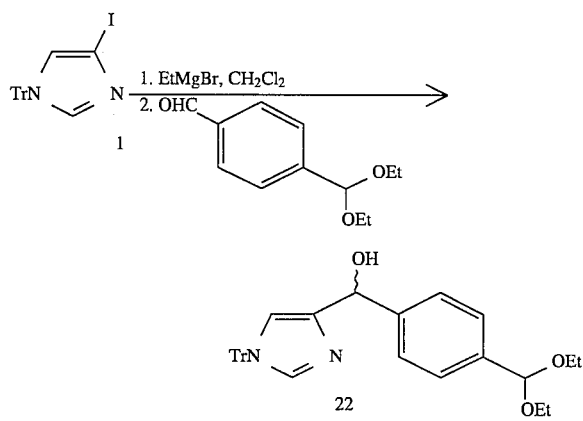

In an analogous manner to that described in Example 1 Part A, compound 22 was obtained in 81% yield by the reaction of the Grignard reagent derived from 1 and terephthalaldehyde mono-(diethylacetal).

Part B.

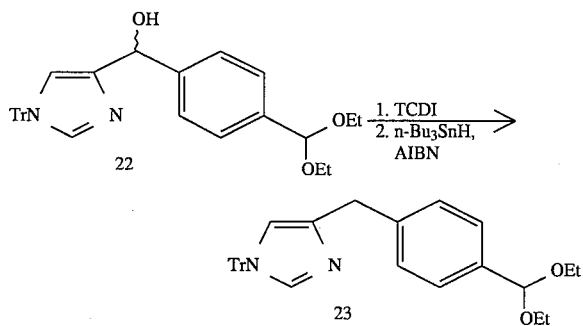

In a manner similar to that described in Example 1 Part B above, compound 23 was derived from compound 22 in 36% overall yield.

Part C.

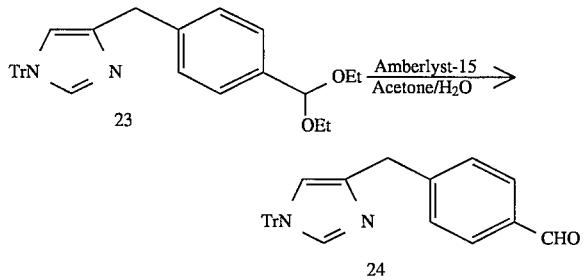

To a solution of 23 (1.37 g, 2.73 mmol) in acetone (15 mL) was added Amberlyst-15 resin (0.15 g) and water (0.2 mL). The reaction was stirred overnight at room temperature and filtered, and the resin washed with additional acetone (25 mL). After drying (MgSO$_4$) and concentration, a white solid was obtained (1.03 g, 88%) that was used without further purification.

Part D.

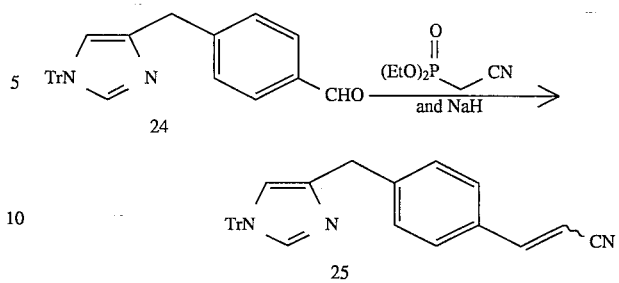

Neat diethyl cyanomethylphosphonate (2.6 mMol, 0.46 g) was added dropwise over 10 min to a pentane-washed suspension of NaH (0.104 g of a 60% suspension in mineral oil, 2.6 mmol) in THF (30 mL) under argon at 0° C. After 45 min., aldehyde 24 (0.86 g, 2 mmol) in THF (30 mL) was added and the reaction stirred for 4 hours. The reaction was poured into water and extracted with chloroform (3×75 mL). The combined organic layers were washed with 12% NaOH, dried (MgSO$_4$), and concentrated. The crude olefins 25 were purified on a flash column (150 g SiO$_2$; 90:10 ether:hexane) to give 0.63 g of a 7.5:1 trans:cis mixture of olefins (70%).

Part E.

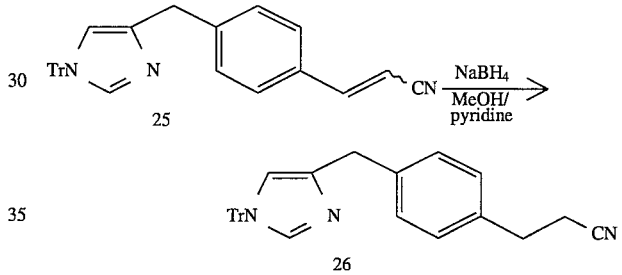

To a solution of 25 (0.43 g, 0.95 mmol) in methanol (0.5 mL) and pyridine (1.5 mL) was added NaBH$_4$ (0.04 g, 1.05 mmol) portionwise. The reaction was heated to 120° C. for 36 hours, cooled and poured into saturated aqueous NH$_4$Cl. The aqueous layer was extracted with ethyl acetate, and the combined organic layers were dried with MgSO$_4$. Filtration and concentration on the rotary evaporator gave a thick oil which was purified on a flash column (75 g SiO$_2$; ether) to give 0.3 g (70%) of 26.

Part F.

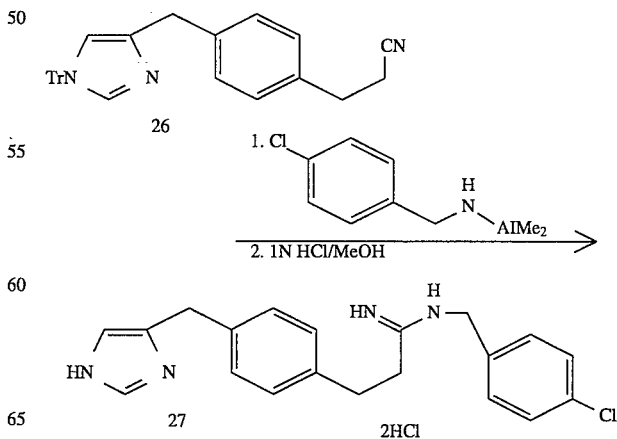

In an analogous manner to that described in Example 1 parts C and D above, compound 26 was transformed into compound 27 (36% overall yield).

Example 9

N-[(4-Chlorophenyl)methyl]-4-[(1H-imidazol-4-yl)methyl]benzene ethanimidamide (as dihydrochloride)

Part A.

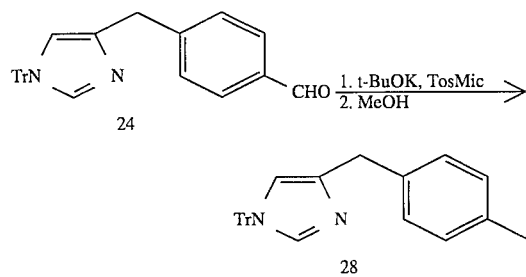

To a solution of t-BuOK in THF (6.5 mL of a 1M solution) at −40° C. was added a solution of TosMic (tosylmethylisocyanide) (0.66 g, 3.4 mmol) in THF (5 mL) followed by the aldehyde 24 (1.31 g, 3.1 mmol) in THF (5 mL). After 1 hour at this temperature, MeOH (10 mL) was added and the reaction heated to reflux for 20 min. It was then cooled to room temperature and the solvent removed under a stream of nitrogen. The residue was dissolved in CH$_2$Cl$_2$ and washed with water/acetic acid (10 mL/0.4 mL). The aqueous layer was extracted with CH$_2$Cl$_2$, and the combined organic layers were washed with aqueous NaHCO$_3$ and dried (MgSO$_4$). The residue obtained upon filtration and evaporation was purified on a flash column (85:15 hexane:isopropanol) to give 0.55 g (40%) of 28.

Part B.

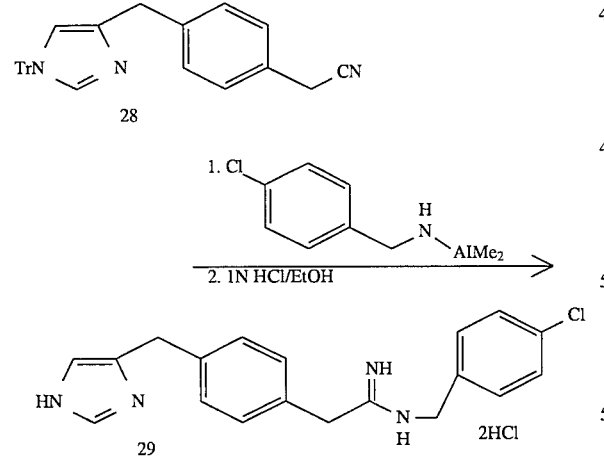

In a manner analogous to that described in Example 1 Parts C and D above, compound 28 was converted into compound 29.

Example 10

4-Chloro-N-[[4-[(1H-imidazol-4-ylmethyl]phenyl]methyl]benzamide

Part A.

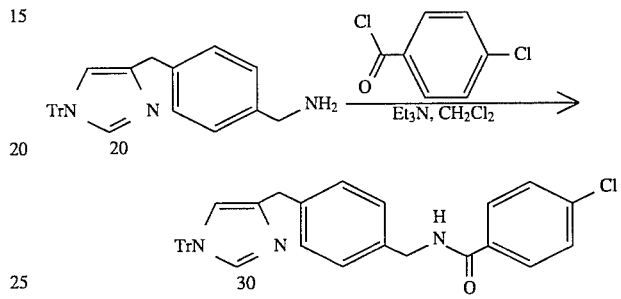

Distilled Et$_3$N (0.25 g, 2.5 mmol) was added to a solution of 20 (0.43 g, 1.0 mmol) in dry methylene chloride (10 mL). The solution was cooled in an ice water bath, and 4-chlorobenzoyl chloride (0.19 g, 1.1 mmol) was added slowly (25 min.). After 1 hour, the reaction was poured into ice-water and extracted with methylene chloride (2×50 mL). The combined organic layers were washed with brine, dried (MgSO$_4$), and concentrated to give a white solid that was purified by flash column chromatography (95:5 methylene chloride: methanol/NH$_3$). Compound 30 was obtained as a white solid (0.55 g, 97%).

Part B.

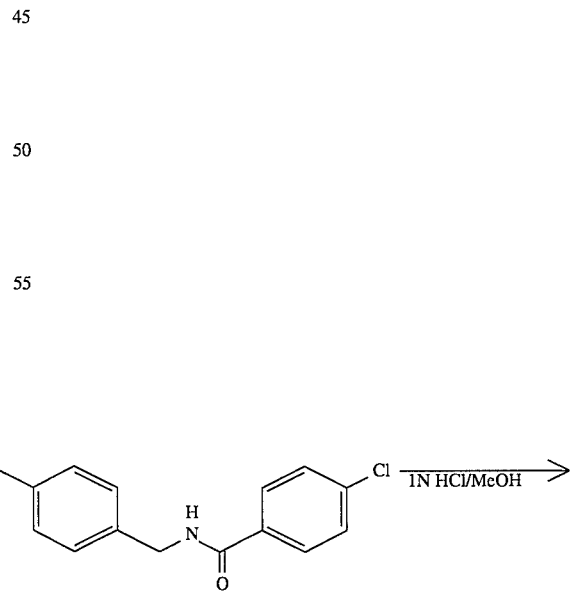

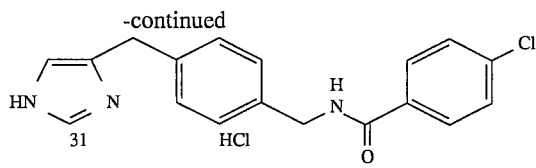

In a manner analogous to that described in Example 1, Part D, Compound 30 was transformed into compound 31.

Example 11

N-[(4-Chlorophenyl)methyl]-4-(1H-imidazol-4-ylmethyl)benzamide

Part A

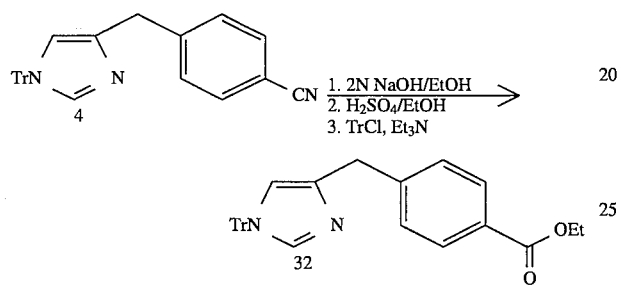

Compound 4 (3 g, 7.1 mmol), 2N NaOH (7.5 mL), and ethanol (35 mL) were heated to reflux for 20 hours. The reaction mixture was cooled to room temperature and concentrated to a paste. Ethanol (50 mL) was added and the mixture concentrated again. This procedure was repeated with toluene. Sulfuric acid (3 mL) and ethanol (30 mL) were added to the residue, and the mixture was heated to reflux for 20 hours. The reaction mixture was cooled to room temperature and adjusted to pH 8 with 2N NaOH. Water was added, and the aqueous mixture extracted with methylene chloride (4×35 mL). The combined organic layers were dried and concentrated. The crude product was redissolved in dry methylene chloride (60 mL) and triethylamine (1.96 mL), and trityl chloride (2.34 g) were added. After 4 hours, additional methylene chloride (100 mL) was added and the reaction mixture was washed with water and brine. The crude material obtained upon drying and concentration was purified on a flash column (ether) to give 32 as a white solid (1.9 g, 57%).

Part B

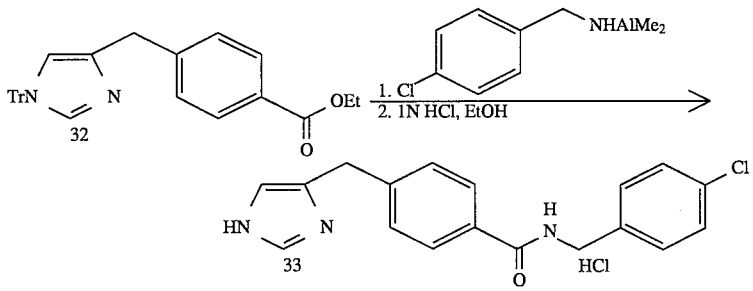

In a manner analogous to that described in Example 1 Parts C and D above, compound 32 was converted into compound 33.

Example 12

4-[[4-[[(4-Chlorophenyl)methoxy]methyl]phenyl]methyl]-1H-imidazole

Part A

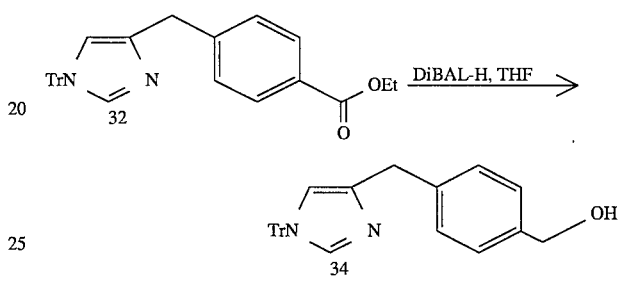

DiBAL-H was added dropwise over 3 min. to a solution of 32 (1 g, 2.1 mmol) in dry THF (14 mL) at 0° C. After 30 min., the reaction was quenched by the slow addition of 2N NaOH. The reaction mixture was poured into ether (60 mL) and additional 2N NaOH (1.5 mL) and water (1.5 mL) were added. After stirring for 10 min., the turbid mixture was washed with water. The water layer was back-extracted with additional ether (25 mL), and the combined ether layers were dried (MgSO$_4$). The crude material was purified on a flash column (ether) to give 0.84 g (93%) of 34 as a white solid.

Part B.

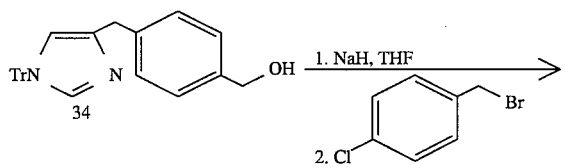

35
-continued

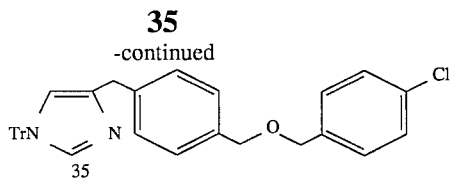

36
-continued

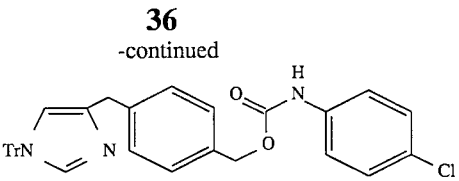

NaH (0.032 g of a 60% dispersion in mineral oil, 0.8 mmol) was added to a solution of 34 (0.26 g, 0.6 mmol) in dry THF (5 mL) at 0° C. The reaction was allowed to warm to room temperature and then stirred for 20 min.; it was then recooled to 0° C., and 4-chlorobenzyl bromide (0.12 g, 0.6 mmol) was added. The reaction was slowly warmed to room temperature and stirred overnight. Additional NaH (0.008 g) and 4-chlorobenzyl bromide (0.041 g) were added and the reaction mixture was stirred an additional 6 hours. The reaction was diluted with ether and washed with water and brine. After drying (MgSO$_4$), the crude material was purified on a flash column (90:10 ether:hexane) to give 35 as a white solid (0.15 g, 46%).

Part C

4-Chlorophenyl isocyanate (0.1 g, 0.66 mmol) was slowly added to a solution of 34 (0.26 g, 0.6 mmol) in dry pyridine (4 mL) at 0° C. When TLC (ether) indicated complete reaction, the pyridine was removed under reduced pressure. The residue was dissolved in methylene chloride (50 mL) and washed with saturated aqueous NaHCO$_3$ and water and dried (MgSO$_4$). The residue obtained upon concentrating was purified on a flash column (80:20 ether:hexane) to give 0.15 g (43%) of 37 as a white solid.

Part B

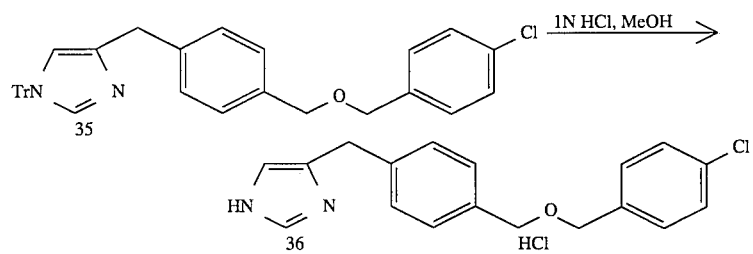

In a manner analogous to that described in Example 1, Part D, 35 compound was transformed into compound 36.

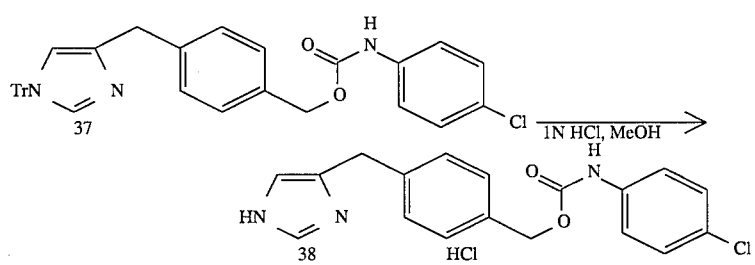

Example 13

[4-(1H-Imidazol-4-ylmethyl)phenyl]methyl N-(4-chlorophenyl)carbamate

Part A

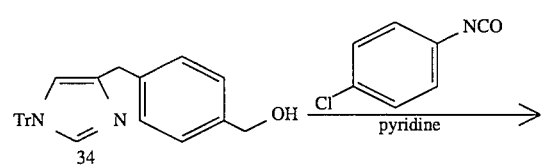

In a manner analogous to that described in Example 1, Part D, compound 37 was transformed into compound 38.

Example 14

[4-(1H-Imidazol-4-ylmethyl)phenyl]methyl 4-chlorobenzoate

Part A

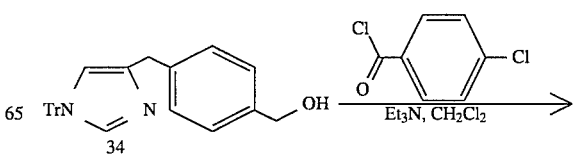

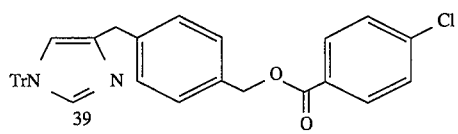

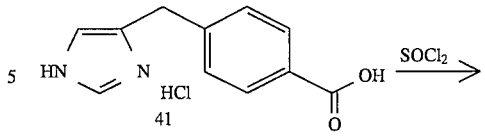

4-Chlorobenzoyl chloride (0.12 g, 0.66 mmol) was slowly added over 20 min. to a solution of 34 (0.26 g, 0.6 mmol) and triethylamine (0.15 g, 1.5 mmol) in dry methylene chloride (10 mL) at 0° C. After 30 min., the reaction was diluted with additional methylene chloride (30 mL) and poured into half-saturated NaHCO$_3$ (20 mL). The organic layer was separated, and the aqueous layer was further extracted with methylene chloride (25 mL). The combined organic layers were dried (MgSO$_4$) and concentrated to give a foam that was purified on a flash column (80:20 ether:hexane). Compound 39 (0.22 g, 64%) was obtained as a white solid.

Part B

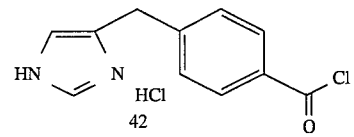

The residue from Part A was suspended in SOCl$_2$ (20 mL) and stirred for 20 hours at room temperature. The excess SOCl$_2$ was removed under reduced pressure and the residue dried by azeotropic removal of toluene. The resulting yellow solid was used directly in the next step without purification.

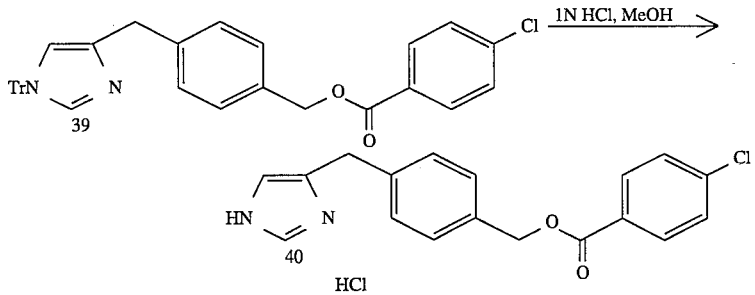

In a manner analogous to that described in Example 1, Part D, compound 39 was transformed into compound 40.

Example 15

(4-Chlorophenyl)methyl 4-(1H-imidazol-4-ylmethyl)benzoate

Part A

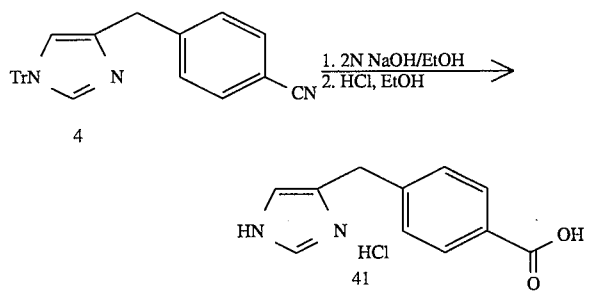

A suspension of 4 (1 g, 2.4 mmol) in ethanol (5 mL) and 2N NaOH (5 mL) was heated to reflux for 20 hours. After cooling, the solvent was removed under reduced pressure and the residue was suspended in 1N HCl (25 mL) and heated to 60° C. for 2 hours. The remaining solid was removed by filtration after cooling, and the aqueous layer was concentrated to give a solid. This was used in the next step without purification.

Part C

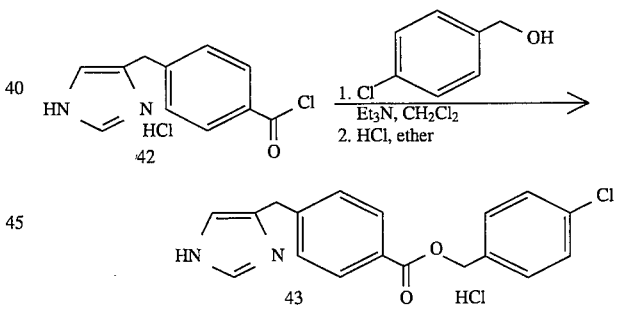

4-Chlorobenzyl alcohol (0.71 g, 5 mmol) and triethylamine (1.01 g, 10 mmol) were added to a suspension of the acid chloride from Part B in dry methylene chloride (15 mL) at 0° C. The reaction mixture was warmed to room temperature and stirred for 24 hours. Additional methylene chloride (50 mL) was added and the organic layer was washed with saturated aqueous NaHCO$_3$. The organic layer was separated and dried (MgSO$_4$). Concentration gave an amber oil that was purified on a flash column (97:3 CH$_2$Cl$_2$:MeOH/NH$_3$). A white solid was obtained (0.36 g, 46% from nitrile 4). This material was dissolved in methylene chloride (10 mL) and 1N HCl in ether (5 mL) was added. The solvent was evaporated under a stream of dry argon to give 43 as a white solid (0.4 g, 100%).

Other compounds named herein can be prepared analogously, together with the following compounds:

N-[(4-chlorophenyl)methyl]-2-fluoro-4-[(1H-imidazol-4-yl)methyl]benzene methanimidamide;

N-[(4-chlorophenyl)methyl]-2-chloro-4-[(1H-imidazol-4-yl)methyl]benzene ethanimidamide;

N-[(4-chlorophenyl)methyl]-3-methyl-4-[(1H-imidazol-4-yl)methyl]benzene methanimidamide;

N-[(4-chlorophenyl)methyl]-2-(1-propenyl)-4-[(1H-imidazol-4-yl)methyl]benzene ethanimidamide;

N-[(4-chlorophenyl)methyl]-3-trifluoromethyl-4-[(1H-imidazol-4-yl)methyl]benzene methanimidamide;

N-[(4-chlorophenyl)methyl]-2-(1-propynyl)-4-[(1H-imidazol-4-yl)methyl]benzene ethanimidamide;

N-[(4-chlorophenyl)methyl]-3-methoxy-4-[(1H-imidazol-4-yl)methyl]benzene methanimidamide;

N-[(4-chlorophenyl)methyl]-2-dimethylamino-4-[(1H-imidazol-4-yl)methyl]benzene ethanimidamide; and N-[(4-chlorophenyl)methyl]-3-methylthio-4-[(1H-imidazol-4-yl)methyl]benzene methanimidamide.

TABLE 2

MASS SPECTRAL DATA FOR COMPOUNDS OF THE EXAMPLES:

| Compound Number | Mass Spectrum | | Compound Number | Mass Spectrum | |
|---|---|---|---|---|---|
| 6 | Calc: | 325.1220 | 21 | Calc: | 187.1109 |
|  | Found: | 325.1231 |  | Found: | 187.1122 |
| 6a | Calc: | 320.1637 | 27 | Calc: | 352.1455 |
|  | Found: | 320.1620 |  | Found: | 352.1476 |
| 6b | Calc: | 358.1404 | 29 | Calc: | 338.1298 |
|  | Found: | 358.1411 |  | Found: | 338.1314 |
| 6c | Calc: | 291.1484 | 31 | Calc: | 326.1060 |
|  | Found: | 291.1500 |  | Found: | 326.1059 |
| 6d | Calc: | 304.1688 | 33 | Calc: | 326.1060 |
|  | Found: | 304.1702 |  | Found: | 326.1059 |
| 9 | Calc: | 200.1062 | 36 | Calc: | 313.1108 |
|  | Found: | 200.1074 |  | Found: | 313.1108 |
| 10 | Calc: | 201.1140 | 38 | Calc: | 342.1009 |
|  | Found: | 201.1152 |  | Found: | 342.0998 |
| 16 | Calc: | 215.1297 | 40 | Calc: | 327.0900 |
|  | Found: | 215.1305 |  | Found: | 327.0891 |
| 17 | Calc: | 215.1297 | 43 | Calc: | 327.0900 |
|  | Found: | 215.1292 |  | Found: | 327.0897 |

$H_3$ Receptor Binding $H_3$ Receptor Binding Assay

The source of the $H_3$ receptors in this experiment was guinea pig brain. The animals weighed 400–600 g. The brain tissue was homogenized using a Polytron in a solution of 50 mM Tris, pH 7.5. The final concentration of tissue in the homogenization buffer was 10% w/v. The homogenates were centrifuged at 1,000× g for 10 min. in order to remove clumps of tissue and debris. The resulting supernatants were then centrifuged at 50,000× g for 20 min. in order to sediment the membranes, which were next washed three times in homogenization buffer (50,000× g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/mL with 0.1% DMSO. Membranes were then added (400 μg of protein) to the reaction tubes. The reaction was started by the addition of 3 nM [$^3$H]R-α-methylhistamine (8.8 Ci/mmol) or 3 nM [$^3$H]N$^α$-methylhistamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (μM). The results are given in Table 3 and Table 4.

TABLE 3

| $K_i$ (μM) values | | | | | |
|---|---|---|---|---|---|
| Compound Number | $K_i$ (μM) | Compound Number | $K_i$ (μM) | Compound Number | $K_i$ (μM) |
| 6 | 0.0140 | 9 | 0.038 | 21 | 0.078 |
| 6a | 0.56 | 10 | 0.31 | 27 | 0.18 |
| 6b | 0.14 | 16 | 0.22 | 29 | 0.0072 |
| 6d | 0.45 | 17 | 0.17 | 38 | 0.024 |

TABLE 4

| Inhibition of binding of radioactive ligand | | | |
|---|---|---|---|
| Compound Number | Inhibition (%) at 2 μg/ml | Compound Number | Inhibition (%) at 2 μg/ml |
| 6c | 48 | 36 | 6–87 |
| 30 | 61 | 40 | 10 |
| 33 | 61 | 43 | 16–78 |

From these test results and the background knowledge about the compounds described in the references in the section "Background of the Invention", it is to be expected that the compounds of the invention would be useful in treating inflammation, allergy, diseases of the GI-tract, cardiovascular disease, or disturbances of the central nervous system.

Pharmaceutically acceptable inert carriers used for preparing pharmaceutical compositions from the compounds of Formula I and their salts can be either solid or liquid. Solid form preparations include powders, tablets, dispersible granules, capsules, cachets and suppositories. The powders and tablets may comprise from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

Liquid form preparations include solutions, suspensions and emulsions, for example water or water-propylene glycol solutions for parenteral injection. Liquid form preparations may also include solutions for intranasal administration.

Also included are solid form preparations which are intended for conversion, shortly before use, into liquid form preparations for either oral or parenteral administration. Such liquid forms include solutions, suspensions and emulsions.

Aerosol preparations suitable for inhalation may include solutions and solids in powder form, which may be in combination with a pharmaceutically acceptable carrier, such as an inert compressed gas.

For preparing suppositories, a low melting wax such as a mixture of fatty acid glycerides or cocoa butter is first melted, and the active ingredient is dispersed homogeneously therein as by stirring. The molten homogeneous mixture is then poured into conveniently sized molds, and allowed to cool and thereby solidify.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose. The quantity of active compound in a unit dose of preparation may be varied or adjusted from about 0.1 mg to 1000 mg, more preferably from about 1 mg to 500 mg, according to the particular application.

The actual dosage employed may be varied depending upon the requirements of the patient and the severity of the condition being treated. The determination of the proper dosage for a particular condition is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgement of the attending clinician considering such factors as age, condition and size of the patient as well as severity of the symptoms being treated. A typical recommended dosage regimen is oral administration of from 1 mg to 2000 mg/day, preferably 10 to 1000 mg/day, in one to four divided doses to achieve relief of the symptoms. The compounds are non-toxic when administered at therapeutic doses.

The following are examples of pharmaceutical dosage forms which contain a compound of the invention. As used therein, the term "active compound" is used to designate one of the compounds of the formula I or salt thereof, especially compounds 6 and 29 herein (as free base), namely N-[(4-chlorophenyl)methyl]-4-[(1H-imidazol-4-yl)methyl]benzene methanimidamide and N-[(4-chlorophenyl)methyl]-4-[(1H-imidazol-4-yl)methyl]benzene ethanimidamide, or the dihydrochloride thereof, but any other compound of the formula I or salt thereof can be substituted therefor:

Pharmaceutical Dosage Form Examples

EXAMPLE A

| | Tablets | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Items No. 1 and 2 in a suitable mixer for 10 to 15 minutes. Granulate the mixture with Item No. 3. Mill the damp granules through a coarse screen (e.g., ¼, 0.63 cm) if necessary. Dry the damp granules. Screen the dried granules if necessary and mix with Item No. 4 and mix for 10–15 minutes. Add Item No. 5 and mix for 1 to 3 minutes. Compress the mixture to appropriate size and weigh on a suitable tablet machine.

EXAMPLE B

| | Capsules | | |
|---|---|---|---|
| No. | Ingredients | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Items No. 1, 2 and 3 in a suitable blender for 10 to 15 minutes. Add Item No. 4 and mix for 1 to 3 minutes. Fill the mixture into suitable two-piece hard gelatin capsules on a suitable encapsulating machine.

While a number of embodiments of this invention are described herein, it is apparent that the embodiments can be altered to provide other embodiments that utilize the compositions and processes of this invention. Therefore, it will be appreciated that the scope of this invention includes alternative embodiments and variations which are defined in the foregoing Specification and by the Claims appended hereto; and the invention is not to be limited to the specific embodiments that have been presented herein by way of example.

We claim:

1. A compound of the formula

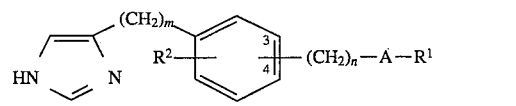

wherein:

A is selected from —O—CO—NR$^1$—, —O—CO—, —NR$^1$—CO—NR$^1$—, —NR$^1$—CO—, —CH$_2$—NR$^1$, and —C(:NR$^1$)—NR$^1$—;

the groups R$^1$, which may be the same or different when there are two or three such groups, are selected from hydrogen, lower alkyl, aryl, cycloalkyl, heterocyclic and heterocyclyl-alkyl groups, and a group of the formula —(CH$_2$)$_y$—G, where G is selected from CO$_2$R$^3$, COR$^3$, CONR$^3$R$^4$, OR$^3$, SR$^3$, NR$^3$R$^4$, heteroaryl and phenyl, which phenyl is optionally substituted by halogen, lower alkoxy or polyhaloloweralkyl, and y is an integer from 1 to 3;

R$^2$ is selected from hydrogen and halogen atoms, alkyl, alkenyl, alkynyl and trifluoromethyl groups, and groups of the formula OR$^3$, SR$^3$ and NR$^3$R$^4$;

R$^3$ and R$^4$ are independently selected from hydrogen, lower alkyl and cycloalkyl groups, or R$^3$ and R$^4$ together with the intervening nitrogen atom may form a saturated ring containing 4 to 6 carbon atoms that may be substituted with one or two lower alkyl groups;

with the proviso that, when y is 1 and G is OR$^3$, SR$^3$ or NR$^3$R$^4$, then neither R$^3$ nor R$^4$ is hydrogen;

the group —(CH$_2$)$_n$—A—R$^1$ is at the 4-position, and the group R$^2$ is at any free position;

with the proviso that, when A is the group —CH$_2$—NR$^1$— or —C(:NR$^1$)—NR$^1$—, the group —(CH$_2$)$_n$—A—R$^1$ is at the 3- or 4-position;

m is an integer from 1 to 3;

and n is 0 or an integer from 1 to 3;

or a pharmaceutically acceptable acid addition salt thereof;

or a pharmaceutically acceptable salt thereof with a base when G is $CO_2H$;
including a tautomeric form thereof.

2. A compound having the formula

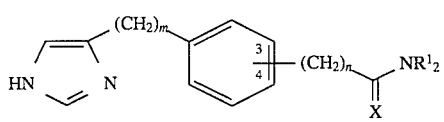

IC wherein:

$X$ is $H_2$ or NH;

the groups $R^1$, which may be the same or different when there are two or three such groups are selected from hydrogen, lower alkyl, aryl, cycloalkyl, and heterocyclic groups, and a group of the formula $—(CH_2)_y—G$, where G is selected from $CO_2R^3$, $COR^3$, $CONR^3R^4$, $OR^3$, $SR^3$, $NR^3R^4$, heteroaryl and phenyl, which phenyl is optionally substituted by halogen, lower alkoxy or polyhaloloweralkyl, and y is an integer from 1 to 3;

m, n, $R^3$ and $R^4$ are as defined in claim 1;

the group $—(CH_2)_n—CX—NR^1{}_2$ is at the 3- or 4-position;

or a pharmaceutically acceptable acid addition salt thereof;

or a pharmaceutically acceptable salt thereof with a base when G is $CO_2H$;

including a tautomeric form thereof.

3. A compound as claimed in claim 2 wherein m is 1 or 2 and n is 0, 1 or 2.

4. A compound as claimed in claim 3 having the

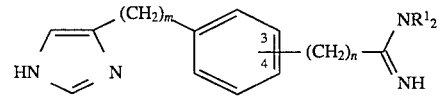

IB

5. A compound of the formula IB defined in claim 4 wherein the side chain $—(CH_2)_n—C(=NH)NR^1{}_2$ is at the 4-position.

6. A compound as claimed in claim 5 wherein the groups $R^1$, which may be the same or different, are selected from hydrogen, aryl groups, and a group of the formula $—(CH_2)_y—G$, where G is selected from pyridyl and phenyl, which phenyl is optionally substituted by halogen, lower alkoxy or polyhaloloweralkyl, and y is 1 or 2.

7. A compound as claimed in claim 6 wherein one of the groups $R^1$ is selected from hydrogen, 4-chlorophenylmethyl, 4-methoxyphenylmethyl, 2-phenylethyl, 4-trifluoromethylphenylmethyl and 4-pyridylmethyl, and the other is a hydrogen atom.

8. A compound as claimed in claim 1 wherein A is $—O—CO—NR^1—$.

9. A compound as claimed in claim 8 wherein the groups $R^1$, which may be the same or different, are selected from hydrogen, aryl groups, and a group of the formula $—(CH_2)_y—G$, where G is selected from pyridyl and phenyl, which phenyl is optionally substituted by halogen, lower alkoxy or polyhaloloweralkyl, and y is 1 or 2.

10. A compound as claimed in claim 9 wherein one of the groups $R^1$ is selected from hydrogen, 4-chlorophenylmethyl, 4-methoxyphenylmethyl, 2-phenylethyl, 4-trifluoromethylphenylmethyl and 4-pyridylmethyl, and the other is a hydrogen atom.

11. A compound as claimed in claim 1 having the formula

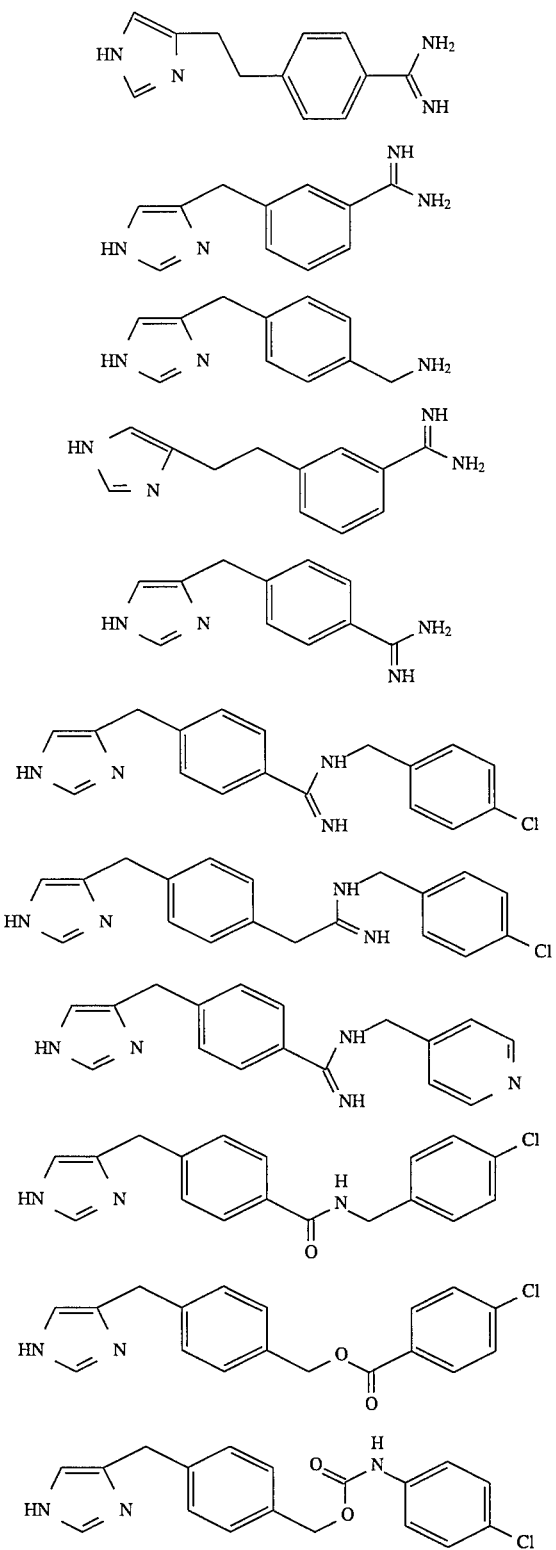

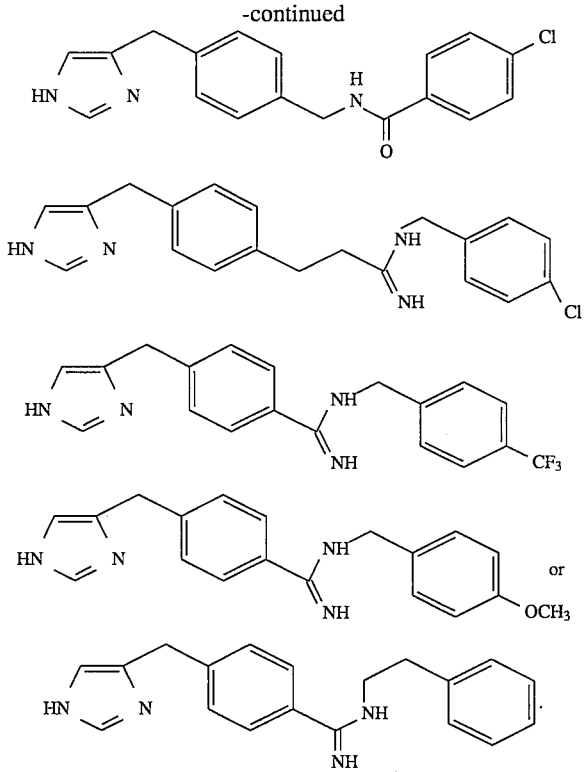

12. A compound of claim 1, having the name N-[(4-chlorophenyl)methyl]-4-[(1H-imidazol-4-yl)methyl]benzene methanimidamide and the structure:

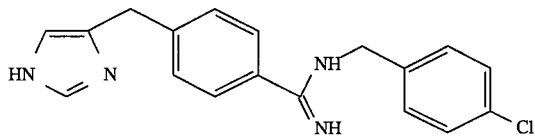

or a pharmaceutically acceptable acid addition salt thereof.

13. A compound of claim 1, having the name N-[(4-chlorophenyl)methyl]-4-[(1H-imidazol-4-yl)methyl]benzene ethanimidamide and the structure:

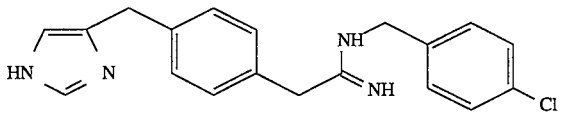

or a pharmaceutically acceptable acid addition salt thereof.

14. A dihydrochloride of the compound of claim 12.

15. The dihydrochloride of the compound of claim 13.

16. A pharmaceutical composition containing as active ingredient a compound of the formula I defined in claim 1 or a pharmaceutically acceptable acid addition salt thereof or a pharmaceutically acceptable salt thereof with a base when G is CO₂H, together with a pharmaceutical carrier or excipient.

17. A method for treating inflammation, which comprises administering to a patient suffering from inflammation an effective amount of a compound or salt as claimed in claim 1.

18. A method for treating allergy, which comprises administering to a patient suffering from allergy an effective amount of a compound or salt as claimed in claim 1.

19. A method for treating diseases of the GI-tract, which comprises administering to a patient suffering from a disease of the GI-tract an effective amount of a compound or salt as claimed in claim 1.

20. A method for treating cardiovascular disease, which comprises administering to a patient suffering from cardiovascular disease an effective amount of a compound or salt as claimed in claim 1.

21. A method of treating sleep disturbances, convulsions, depression, or disturbances of hypothalamo-hypophyseal secretions, which comprises administering to a patient suffering from sleep disturbances, convulsions, depression, or disturbances of hypothalamo-hypophyseal secretions an effective amount of a compound or salt of the formula

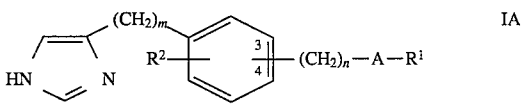

wherein:

A is selected from —O—CO—NR¹, —O—CO—, —NR¹—CO—NR¹—, —NR¹—CO—, —CO—NR¹—, —COO—, —CH₂—NR¹— and —C(:NR¹)—NR¹—;

the groups R¹, which may be the same or different when there are two or three such groups are selected from hydrogen, lower alkyl, aryl, cycloalkyl, heterocyclic and heterocyclyl-alkyl groups, and a group of the formula —(CH₂)$_y$—G, where G is selected from CO₂R³, COR³, CONR³R⁴, OR³, SR³, NR³R⁴, heteroaryl and phenyl, which phenyl is optionally substituted by halogen, lower alkoxy or polyhaloloweralkyl, and y is an integer from 1 to 3;

R² is selected from hydrogen and halogen atoms, alkyl, alkenyl, alkynyl and trifluoromethyl groups, and groups of the formula OR³, SR³ and NR³R⁴;

R³ and R⁴ are independently selected from hydrogen, and lower alkyl and cycloalkyl groups, or R³ and R⁴ together with the intervening nitrogen atom may form a saturated ring containing 4 to 6 carbon atoms that may be substituted with one or two lower alkyl groups;

with the proviso that, when y is 1 and G is OR³, SR³ or NR³R⁴, then neither R³ nor R⁴ is hydrogen;

the group —(CH₂)$_n$—A—R¹ is at the 4-position, and the group R² is at any free position;

with the proviso that, when A is the group —CH₂—NR¹—, the group —(CH₂)$_n$—A—R¹ is at the 3- or 4-position;

m is an integer from 1 to 3;

and n is 0 or an integer from 1 to 3;

or a pharmaceutically acceptable acid addition salt thereof;

or a pharmaceutically acceptable salt thereof with a base when G is CO₂H;

including a tautomeric form thereof.

* * * * *